US009896489B2

(12) United States Patent
Johnson et al.

(10) Patent No.: US 9,896,489 B2
(45) Date of Patent: Feb. 20, 2018

(54) FAMILY OF SYNTHETIC POLYNUCLEOTIDE-BINDING PEPTIDES AND USES THEREOF

(71) Applicant: Eastern Virginia Medical School, Norfolk, VA (US)

(72) Inventors: Edward M. Johnson, Norfolk, VA (US); Dianne C. Daniel, Norfolk, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 0 days.

(21) Appl. No.: 14/433,160

(22) PCT Filed: Oct. 3, 2013

(86) PCT No.: PCT/US2013/063330
§ 371 (c)(1),
(2) Date: Apr. 2, 2015

(87) PCT Pub. No.: WO2014/055800
PCT Pub. Date: Apr. 10, 2014

(65) Prior Publication Data
US 2016/0052979 A1    Feb. 25, 2016

Related U.S. Application Data

(60) Provisional application No. 61/710,447, filed on Oct. 5, 2012.

(51) Int. Cl.
*C07K 14/00* (2006.01)
*C07K 14/47* (2006.01)
*A61K 38/00* (2006.01)

(52) U.S. Cl.
CPC .......... *C07K 14/4702* (2013.01); *C07K 14/00* (2013.01); *A61K 38/00* (2013.01)

(58) Field of Classification Search
None
See application file for complete search history.

(56) References Cited

U.S. PATENT DOCUMENTS 5,672,479 A    9/1997    Johnson et al.

FOREIGN PATENT DOCUMENTS

WO    WO-2004/026120    4/2004
WO    WO-2008/063113    5/2008

OTHER PUBLICATIONS

National Cancer Institute, "Understanding Cancer Prognosis", http://www.cancer.gov/aboutcancer/diagnosisstaging/prognosis#cureremissiondifference; pp. 1-7 accessed Jun. 2, 2016.*
American Cancer Society, Can advanced or metastatic cancer be prevented?, http://www.cancer.org/treatment/understanding yourdiagnosis/advancedcancer/advancedcancerprevention1, 2014, pp. 1-2; accessed Jun. 2, 2016.*
Thundimadathil, "Cancer Treatment Using peptides: Current Therapies and Future Prospects", Journal of Amino Acids, 2012, pp. 1-13.*
Arya, Human Immunodeficiency Virus Type 2 (HIV-2) Trans-Activator (Tat): Functional Domains and the Search for Trans-Dominant Negative Mutants, Aids Research and Human Retroviruses, 1993, pp. 839-848.*
Fitzgerald et al., "Dietary ω-3 polyunsaturated fatty acid intake and risk for amyotrophic lateral sclerosis", JAMA Neurology, 2014, pp. 1102-1110.*
Healthline Networks , "Fragile X Syndrome", http://www.healthline.com/health/fragile-x-syndrome, accessed on Jun. 10, 2016.*
Gen Bank Accession No. NP_005850;https://www.ncbi.nlm.nih.gov/protein/NP_005850; pp. 1-5; 1992; accessed on Mar. 23, 2017.*
Bergemann et al., "Sequence of cDNA comprising the human pur gene and sequence-specific single-stranded-DNA-binding properties of the encoded protein," Mol. Cell. Biol. 12, 5673-5682 (1992).
Bergemann and Johnson, "The HeLa Pur factor binds single-stranded DNA at a specific element conserved in gene flanking regions and origins of DNA replication," Mol. Cell. Biol. 12, 1257-1265 (1992).
Graebsch et al., "X-ray structure of Pur-alpha reveals Whirly-like fold and an unusual nucleic-acid binding surface," Proc. Natl. Acad. Sci. USA 106(44), pp. 18521-18526 (2009).
Johnson, "The Pur protein family: Clues to function from recent studies on cancer and AIDS," Anticancer Res. 23, 2093-2100 (2003).
Lezon-Geyda et al., "Deletions of PURA, at 5q31, and PURB, at 7p13, in myelodysplastic syndrome and progression to acute myelogenous leukemia," Leukemia 15, 954-962 (2001).
Liu et al., "Functional interaction of Puralpha with the Cdk2 moiety of cyclin A/Cdk2," Biochem. Biophys. Res. Commun. 328, 851-857 (2005).
Da Silva et al., "hnRNP-K and Purα act together to repress the transcriptional activity of the CD43 gene promoter," Blood 100, 3536-3544 (2002).
Weinreb et al. "Polyoma virus infection is a prominent risk factor for bladder carcinoma in immunocompetent individuals," Diagnostic Cytopath., 34, 201-203 (2006).
International Search Report and Written Opinion for International Patent Application No. PCT/US13/63330, dated Feb. 10, 2014 (10 pages).

(Continued)

*Primary Examiner* — Lianko Garyu
(74) *Attorney, Agent, or Firm* — Wilmer Cutler Pickering Hale and Dorr LLP

(57) ABSTRACT

The present invention provides novel synthetic peptides (including the TZIP peptide) as oncogenic and genetic modulators, including genetics of viruses, as well as methods of making and using the same. These peptides are useful for inhibiting the proliferation of cancer cells characterized as having amplified c-MYC genes. The invention provides methods for the therapeutic uses of the peptides in the treatment of various cancers including small cell lung carcinoma, prostate cancer, lymphoma, brain tumors, colon cancer, bladder cancer, AML, malignant melanoma, mesothelioma, and cancers of head and neck. The peptides are also useful in the treatment of and prevention of transmission of HIV and treatment of expanded nucleotide repeat diseases, including certain currently untreatable and debilitating diseases.

5 Claims, 12 Drawing Sheets

(56) References Cited

OTHER PUBLICATIONS

Little et al., "Amplification and expression of the c-myc oncogene in human lung cancer cell lines," Nature vol. 306, No. 5939, pp. 194-196 (Abstract only, 1 page) (1983).

National Institute of Neurological Disorders and Stroke, "Neurological Complications of AIDS Fact Sheet," Last updated May 16, 2012 (5 pages) <https://web.archive.org/web/20120822090243/http://www.ninds.nih.gov/disorders/aids/detail_aids.htm>.

Wei et al., "A Single Stranded DNA-Binding Protein, ssCRE-BP/Purα, in Rat Lung and Its Increase in Allergic Airway Inflammation," Japanese Journal of Pharmacology vol. 78, No. 4, pp. 419-427 (1998).

White et al., "Multiple roles for Purα in cellular and viral regulation," Cell Cycle vol. 8, No. 3, pp. 414-420 (2009).

\* cited by examiner

FIG. 10

SYNTHETIC TZIP CODING NUCLEOTIDE

| | | | | | | |
|---|---|---|---|---|---|---|
| 00001 | CCCGTGTAAA | ACGACGGGCCA | GTTTATCCTAG | TCAGCTTGAT | CGTGGACCGG | AAGGTGAGCC | AGTGAGTTGA |
| 00081 | TTGCAGTCCA | GTTACGCTGG | AGTTCGAGGC | TCGTCCTGAA | CCGCCGGAGG | GTTGCGTTTG | AGACGGGCGA |
| 00161 | CAGATCGACA | CTGCTCGATC | CGTCGGCACC | TTTTGAATTC | AGCACCCTTCG | TCACGAGGA | CAACAAGAGG |
| 00241 | TACTTCATGG | ACTTGAAGGA | GAACCAGAGG | GGTAGATTTA | CCAAGTCGGT | ACGAGGGAT | ACAGGAACTC |
| 00321 | CCTCACCGTC | TCCTACTCGG | TCGCATGGCT | CGAGTTCAGG | GTAAGCTCA | CGAGAGTAC | GCAAAGCTCC |
| 00401 | AGTACGCAAG | GGCAAAGAGG | AGACAGGCAA | GAAGGCAGAT | CAGCAGCAA | AGCAGGAGTG | AGTTTAAACT |
| 00481 | TTTGATGA | CGAGCTGGAT | GCCGACTGGA | CAGTTCTCGA | CGAGCAGCT | CCGTGATCTT | ACGGCATTAT |
| 00561 | AGTATGATC | GGTCCACGAT | CAGCAGATT | ATCTAGTCAG | CTTGATGTCA | CTGAGGCTCA | ATACTGACCA |
| 00641 | TTTAAATCAT | ACCTGACCTC | CATAGCAGAA | AGTCAAAAGC | CTCCGACCGG | CTTGATCGGC | AGTAAGAGG |

FIG. 11

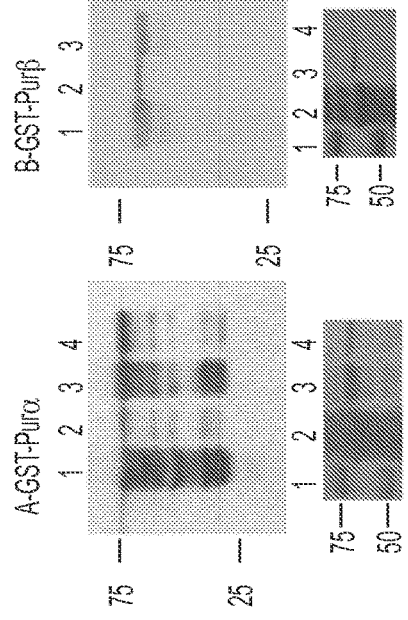

SEQUENCE LISTING

```
<160> NUMBER OF SEQ ID NOS: 12

<210> SEQ ID NO 1
<211> LENGTH: 89
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 1

Leu Ala Ser Thr Phe Val Thr Arg Asp Asn Lys Arg Tyr Phe Met Asp
1               5                   10                  15

Leu Lys Glu Asn Gln Arg Gly Arg Phe Met Arg Val Ser Gln Val Gly
            20                  25                  30

Thr Arg Gly Tyr Arg Asn Ser Leu Thr Val Ser Tyr Ser Val Ala Trp
        35                  40                  45

Leu Glu Phe Arg Thr His Leu Cys Lys Leu Ile Asp Glu Tyr Ala Lys
    50                  55                  60

Leu Gln Tyr Ala Arg Ala Lys Arg Arg Gln Ala Arg Gln Ile Arg
65                  70                  75                  80

Gln Gln Gln Gln Gln Gln Gln Glu Glu
                85

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ala Arg Ala Lys Arg Arg Gln Ala Arg Arg Gln Ile Arg
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Phe Leu Gln Ile Leu Glu Lys Thr Pro Asn Arg Leu Lys Arg Ile Trp
1               5                   10                  15

Asn Trp Arg Ala Cys Glu Ala Ala Lys Lys Thr Lys Ala Asp Asp Arg
            20                  25                  30

Gly Thr Asp Glu Lys Thr Ser Glu Gln Thr Ile Leu Asn Met Ile Ser
        35                  40                  45

Gln Ser Ser Ser Asp
    50

<210> SEQ ID NO 5
<211> LENGTH: 53
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 5

Tyr Arg Asn Ser Leu Thr Val Ser Tyr Ser Val Ala Trp Leu Glu Phe
1               5                   10                  15

Arg Thr His Leu Cys Lys Leu Ile Asp Glu Tyr Ala Lys Leu Gln Tyr
            20                  25                  30

Ala Arg Ala Lys Arg Gln Ala Arg Gln Ile Arg Gln Gln Gln
        35                  40                  45

Gln Gln Gln Gln Glu
    50

<210> SEQ ID NO 6
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Tyr Arg Asn Ser Ile Thr Val Pro Tyr Lys Val Trp Ala Lys Phe Gly
1               5                   10                  15

His Thr Phe Cys Lys Tyr Ser Glu Glu Met Lys Lys Ile Gln Glu Lys
            20                  25                  30

Gln Arg Glu Lys Arg Ala Ala Cys Glu Gln Leu His Gln Gln Gln Gln
        35                  40                  45

Gln Gln Gln Glu
    50

<210> SEQ ID NO 7
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Gly Arg Pro Lys Glu Lys Ser Leu Val Leu Val Lys Leu Glu Pro
1               5                   10                  15

Trp Leu Cys Arg Val His Leu Glu Gly Thr Gln Arg Glu Gly Val Ser
            20                  25                  30

Ser Leu Asp Ser Ser Ser Leu Ser Leu Cys Leu Ser Ser Ala Asn Ser
        35                  40                  45

Leu Tyr Asp
    50

<210> SEQ ID NO 8
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Ser Ala Gly Arg Pro Lys Glu Lys Ser Leu Val Leu Val Lys Leu
1               5                   10                  15

Glu Pro Trp Leu Cys Arg Val His Leu Glu Gly Thr Gln Arg Glu Gly
            20                  25                  30
```

```
Val Ser Ser Leu Asp Ser Ser Ser Leu Ser Leu Cys Leu Ser Ser Ala
        35                  40                  45

Asn Ser Leu Tyr Asp
    50

<210> SEQ ID NO 9
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Tyr Arg Asn Ser Leu Thr Val Ser Tyr Ser Val Ala Trp Leu Glu Phe
1               5                   10                  15

Arg Thr His Leu Ala Lys Leu Ile Asp Glu Tyr Ala Lys Leu Gln Tyr
            20                  25                  30

Ala Arg Ala Lys Arg Arg Gln Ala Arg Arg Gln Ile Arg Gln Gln Gln
        35                  40                  45

Gln Gln Gln Gln Glu
    50

<210> SEQ ID NO 10
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Tyr Arg Asn Ser Leu Thr Val Ser Tyr Ser Val Ala Trp Leu Glu Ala
1               5                   10                  15

Arg Thr His Leu Cys Lys Leu Ile Asp Glu Tyr Ala Lys Leu Gln Tyr
            20                  25                  30

Ala Arg Ala Lys Arg Arg Gln Ala Arg Arg Gln Ile Arg Gln Gln Gln
        35                  40                  45

Val Gln Gln Gln Glu
    50

<210> SEQ ID NO 11
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Tyr Arg Asn Ser Arg Thr Lys Ser Tyr Ser Val Ala Trp Leu Glu Phe
1               5                   10                  15

Glu Thr His Leu Cys Lys Leu Ile Asp Glu Tyr Ala Lys Leu Gln Tyr
            20                  25                  30

Ala Arg Ala Lys Arg Arg Gln Ala Arg Arg Gln Ile Arg Gln Gln Gln
        35                  40                  45

Gln Gln Gln Gln Glu
    50

<210> SEQ ID NO 12
<211> LENGTH: 720
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (517)..(517)
<223> OTHER INFORMATION: Inosine
<220> FEATURE:
<221> NAME/KEY: modified_base
<222> LOCATION: (535)..(535)
<223> OTHER INFORMATION: Inosine
<220> FEATURE:
<221> NAME/KEY: modified_base
<222> LOCATION: (603)..(603)
<223> OTHER INFORMATION: Inosine

<400> SEQUENCE: 12
cccgtgtaaa acgacggcca gtttatctag tcagcttgat tctagctgat cgtggaccgg      60
aaggtgagcc agtgagttga ttgcagtcca gttacgctgg agtctgaggc tcgtcctgaa     120
tgatatgcga ccgccggagg gttgcgtttg agacgggcga cagatcgaca ctgctcgatc     180
cgctcgcacc ttttgaattc tcaactcgca agcaccttcg tcacgaggga caacaagagg     240
tacttcatgg acttgaagga gaaccagagg ggtagattta tgagggtctc ccaagtcggt     300
acgaggggat acaggaactc cctcaccgtc tcctactcgg tcgcatggct cgagttcagg     360
acccacctct gtaagctcat cgacgagtac gcaaagctcc agtacgcaag ggcaaagagg     420
agacaggcaa gaaggcagat caggcagcaa cagcagcaac agcaggagtg agtttaaact     480
tttggatcga cgagagcagc gcgactggat cagttcngga cgagcgagct gtcgnccgac     540
ccgtgatctt acggcattat acgtatgatc ggtccacgat cagctagatt atctagtcag     600
ctngatgtca tagctgtttc ctgaggctca atactgacca tttaaatcat acctgacctc     660
catagcagaa agtcaaaagc ctccgaccgg aggcttttga cttgatcggc acgtaagagg     720
```

FAMILY OF SYNTHETIC POLYNUCLEOTIDE-BINDING PEPTIDES AND USES THEREOF

CROSS REFERENCE TO RELATED APPLICATION

This application is a National Stage of International Application No. PCT/US2013/063330 (published as WO 2014/055800 A1), filed on Oct. 3, 2013, which claims the benefit of U.S. Provisional Application No. 61/710,447, filed on Oct. 5, 2012, the contents of both of which are hereby incorporated by reference.

STATEMENT CONCERNING GOVERNMENT RIGHTS IN FEDERALLY-SPONSORED RESEARCH

This invention was made with government support under Grant No. CA55219, of the National Cancer Institute, National Institutes of Health and Grant No. NS35000, of the National Institute of Neurological Disorders and Stroke, National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Oct. 26, 2015, is named 0113019.00246US5_SL.txt and is 7,868 bytes in size.

FIELD OF THE INVENTION

This invention relates to a family of novel synthetic peptides for the treatment of various diseases and methods of treatment using such peptides. The invention also relates to methods of generating such peptides.

BACKGROUND

Purα (also known as Pur-alpha, Pur-α, or Puralpha), Cyclin T1, and interferon regulatory factors ("IRFs") 3 and 7 are all naturally occurring proteins that are involved in nucleic acid regulatory processes in healthy and unhealthy mammalian cells, including those of humans. They are also involved in the transmission and replication of viral pathogens, including HIV, polyomaviruses and species of bacteria, including those causing Lyme disease and syphilis, as well as protists including those causing malaria. Transactivator of transcription ("Tat") is a HIV gene which, through the involvement of partner proteins (such as Purα, cyclin T1, and IRF3 and 7), increases the level of transcription of HIV DNA. The interactions between Purα, Cyclin T1, and IRFs 3 and 7 with Tat cause HIV transcription and co-opting of cellular functions. There is a need for synthetic agents that will interfere with Tat and these protein binding partners in order to prevent or reduce the spread of HIV infection. In addition, Purα, Cyclin T1, and IRFs 3 and 7 are involved in transcription and cellular processes. For example, Purα is involved in regulating both cell growth and cell fate in cancer. Therefore, there is also a need to harness the beneficial properties of the Purα protein in order to provide therapies to treat or prevent cancers. The common denominator in Purα function, tying together its actions in all organisms, is its ability to bring proteins and nucleic acids together in such a way that these two classes of macromolecules can move relative to each other. A value of this invention is that it can inhibit pathological aspects of Purα function while allowing Purα functions necessary for healthy cell activities. The polypeptides of the invention are also valuable due to their ability to be delivered.

Purα

Purα is a sequence-specific single-stranded DNA-binding protein that functions in binding both DNA and RNA. It binds to purine-rich ("Pur") elements found in the promoters of genes, and has a great affinity for DNA elements upstream of the c-MYC gene (Bergemann, A. D. and Johnson, E. M. (1992) The HeLa Pur factor binds single-stranded DNA at a specific element conserved in gene flanking regions and origins of DNA replication. Mol. Cell. Biol. 12, 1257-1265; Bergemann, A. D., Ma, Z.-W. and Johnson, E. M. (1992) Sequence of cDNA comprising the human pur gene and sequence-specific single-stranded-DNA-binding properties of the encoded protein. Mol. Cell. Biol. 12, 5673-5682; Johnson, E. M., *Anticancer Res.*, 23:2093-2100 (2003)). Purα can act as either a transcriptional activator or a repressor. (D. Silva, N., A. Bharti, and C. S. Shelley, *Blood*, 100:3536-3544 (2002); Gallia, G. L., E. M. Johnson, and K. Khalili, 28:3197-3205 (2000)).

Purα is multifunctional in nature, as it is involved in DNA replication, RNA transcription, RNA transport, viral protein interactions, and regulation of viral replication at low concentrations. More specifically, Purα is involved in regulating both cell growth and cell fate. For example, Purα regulates progression of the cell cycle.

The cell cycle is a sequence of events, including interphase and the mitotic phase, from the time a eukaryotic cell divides to form two daughter cells to the time the daughter cells divide again. The cycle consists of four phases, gap 1 ("$G_1$"), synthesis ("S"), gap 2 ("$G_2$"), and mitosis ("M"). Interphase occurs from $G_1$ phase through the $G_2$ phase. During $G_1$, the cell increases in size, and increases its supply of proteins and the number of many of its organelles (e.g., mitochondria and ribosomes). Following $G_1$, S phase occurs. DNA synthesis (replication) occurs during S phase, and after DNA replication, single chromosomes are present as double chromosome, each consisting of two sister chromatids. The third subphase, $G_2$, spans the time from the completion of DNA synthesis to the beginning of cell division. During this time, proteins that are essential to cell division are made by the cell. During the fourth subphase, M, cytokinesis and mitosis occur. Cytokinesis is the process by which the cytoplasm (cytokinesis) divides and is distributed to form two daughter cells. Mitosis is the process by which the nucleus and its contents, including the duplicated chromosomes, divide and are distributed to form two cells.

The introduction or expression of Purα during various phases of the cell cycle can be used to regulate cell growth. Purα interacts directly with retinoblastoma protein ("Rb"), cyclin-dependent kinase ("Cdk2"), and cell division cycle 6 ("Cdc6") in a dose dependent manner to affect cell determination after oncogenic stress. For example, microinjection of Purα halts deregulated cell growth by arresting cell-cycle progression at the $G_1$ or $G_2$/M phases, depending upon the cell cycle phase during which Purα is injected. During S phase, cyclin A must bind with Cdk2 for the cell to progress normally through the S phase. Purα co-localizes with cyclin A/Cdk2 in S and $G_2$ to interrupt this process. Specifically, Purα recruits Cdk2 to specific Purα binding sites. The interaction of Purα with Cdk2 stimulates histone phosphorylation and displaces the kinase inhibitor, p21, to affect chromatin structure. (Liu, H., S. M. Barr, C. Chu, D.

S. Kohtz, Y. Kinoshita, and E. M. Johnson, *Biochem. Biophys. Res. Commun.*, 328:851-7 (2005)). Purα further alters chromatin structure by binding to Pur elements to cause local unwinding that affects DNA structure upstream and downstream. Thus, Purα has the ability to regulate cell growth by altering chromatin structure.

Cancer

The c-MYC gene is an oncogene that participates in the progression of many cancers. Cancers such as small cell lung carcinoma ("SCLC"), prostate cancer, lymphoma, various brain tumors, colon cancer, and cancers of the head and neck have been found to have amplified c-MYC genes. Expression of the Purα peptide has been shown to block proliferation of a variety of oncologically transformed cells, especially those that exhibit amplified c-MYC genes.

Deletions or monosomy of chromosomes 5 and 7 are frequently observed in myelodysplastic syndromes (MDS) and acute myelogenous leukemia (AML). PURA and PURB are two genes encoding functionally cooperative proteins in the Pur family. Concurrent deletions of PURA and PURB occur in MDS at a rate nearly 1.5-fold higher than statistically expected and in AML at a rate 0.5-fold higher. This novel simultaneous deletion of two closely related gene family may thus have consequences related to progression to AML. Alterations in these genes could affect a delicate balance critical in myeloid development (See Lezon-Geyda, K., Najfeld, V., and Johnson, E., "Deletions of PURA, at 5q31, and PURB, at 7p13, in myelodysplastic syndrome and progression to acute myelogenous leukemia," Leukemia (2001) 15, 954-962, which is incorporated by reference herein in its entirety).

Small Cell Lung Carcinoma

SCLC is closely associated with smoke inhalation, and is one of the deadliest human cancers. This highly invasive cancer affects epithelial cells of the lungs. By the time SCLC is diagnosed, it is usually widely disseminated in the lungs and inoperable. Treatment for SCLC is limited. Although initially sensitive to radiation, the effects of radiation on SCLC are short lived. Moreover, there is no effective chemotherapeutic treatment for this disease. The average life span following diagnosis of SCLC is about six months.

Prostate Cancer

Prostate cancer affects about 16% of males in the United States, a percentage which is projected to increase over the next 20 years. Nearly 30% of men with prostate cancer will experience recurrence after local therapy. Recurrent prostate cancer is mostly androgen-dependent, and thus is responsive to androgen deprivation therapy. However, in many survivors, fatal, androgen-independent hormone refractory prostate cancer with metastases develops.

The progression of prostate cancer is critically linked to levels of the cellular protein, Purα. In the beginning stages, prostate cancer is generally androgen dependent and can be treated with androgen antagonists. After a period of time, however, the tumor becomes androgen independent in a subset of patients. Treatment of androgen-independent prostate cancer is more difficult to treat and frequently leads to metastases and poor prognosis. The switch to the androgen-independent state involves over-expression of the androgen receptor protein due to loss of Purα from the androgen receptor gene transcriptional suppressor ("ARS") complex. An overabundance of androgen receptor protein causes a reduction in androgen specificity. The mechanism by which this occurs, however, is not yet understood. Levels of Purα in the nucleus and bound to the androgen receptor gene ARS element are reduced in the androgen-independent state and in hormone-resistant tumor samples. Restoration of Purα levels by transfection reduces androgen receptor protein levels and reverses the androgen-independent state.

In addition to its involvement in the switch to androgen independence, Purα may also be involved in the initial transformation stages of certain prostate cancer cases. In a study of more than 4,000 immunocompetent patients that had a urine cytology pathology examination, it was found that a diagnosis of polyoma virus infection is a strong risk factor for subsequent diagnosis of prostate cancer (Weinreb, D. B., Desman, G. T., Amolat-Apiado, M. J. M., Burstein, D. E., Godbold, J. H., Jr. and Johnson, E. M. (2006) Polyoma virus infection is a prominent risk factor for bladder carcinoma in immunocompetent individuals. Diagnostic Cytopath., 34, 201-203, which is incorporated by reference herein in its entirety).

It has also been shown that Purα alone inhibits the DNA replication of JCV, a member of the polyoma virus family. Interaction with the HIV-1 Tat protein co-opts Purα activity, and the resulting complex stimulates JCV late gene transcription and DNA replication. Purα has been demonstrated to interact with JCV T-antigen, tumor suppressor protein, Rb, and to reverse inhibition of protein phosphorylation by cyclin-dependent kinase inhibitor p21. Purα levels are high in normal prostate cells and androgen dependent cells. Thus, Purα may have a dual role both in the initiation transforming process of prostate cancer cells, acting as a facilitator of viral effects when at high levels, and in the switch to the androgen independent state, acting as a lost suppressor of androgen receptor expression when at reduced levels.

There is a need to harness the beneficial properties of the Purα protein in order to provide therapies to treat or prevent cancers by specifically targeting cancer cells while minimizing harm to normal, healthy cells.

Human Immunodeficiency Virus (HIV)

HIV has multiple steps in its infective pathway. These mechanisms allow it to enter a host cell and replicate, which if untreated will ultimately result in the death of the host cell and further infection of other cells by the replicated HIV virus. One primary step in HIV's replication involves the transactivation of HIV-1 transcription. Interfering with and/or stopping this step entirely would minimize the spread of the infection in a particular host animal, or it may allow for a mechanism to prevent transmission between hosts. Some particular proteins important for this step include IRF 3 and 7, Cyclin TI and Purα. The Tat protein interacts with IRF 3 and 7 to cause relocalization of these IRFs in neural cells. Tat also interacts with Purα, the crystal structure of which has been published (Graebsch et al., 2009 X-ray structure of Pur-{alpha} reveals Whirley-like fold and an unusual nucleic-acid binding surface. *Proc Natl Acad Sci USA*, which is incorporated by reference herein in its entirety). Data presented in this application provide additional support of the Tat-Purα interaction. Tat also interacts with Cyclin/T1 and the crystal structure of Tat bound to Cyclin T1/Cdk9 has also recently been published (David Price and colleagues). The domain of Tat that binds Cyclin T1, closely resembles that of an active enzyme site. Tat requires for its activities coordination of two Zn ions. Therefore, there is a need to develop proteins which will interfere with Tat's ability to interact with IRF3 and 7, Cyclin T1, and Purα in order to hinder or prevent HIV transcription.

Repeat Expansion Disorders

Repeat expansion disorders are neurodegenerative diseases which involve short nucleotide sequences being repeated at a certain locus many more times than normal. One important disease associated with repeat expansions is amyotrophic lateral sclerosis (ALS), a fatal neurodegenerative disorder that causes progressive damage to motor neurons. A common genetic feature of this disease is the expansion of a GGGGCC repeat. There is currently no treatment for this disease.

As previously described, the Pur family of proteins are nucleic acid binding proteins. There are four identified members of the Pur family, all of which share common structural features. The most important of these is the nucleic acid binding region, which consists of a conserved domain repeated three times. This region binds preferentially to G-rich repeated sequences in nucleic acids, suggesting it may be involved in the etiology of ALS.

The involvement of Pur proteins in repeat expansion disorders may be due to the repeat expansions binding to Pur proteins and sequestering them, preventing them from performing their normal functions. If this were the case, preventing sequestration could prevent the cellular damage caused by repeat expansions. Xu et al. (Xu, Z et al. (2013), "Expanded GGGGCC repeat RNA associated with amyotrophic lateral sclerosis and frontotemporal dementia causes neurodegeneration," *Proceedings of the National Academy of Sciences*, vol 110 (7778-83), which is incorporated by reference herein in its entirety) have recently reported that overexpression of Purα in mouse neuronal cells mitigates certain aspects of rGGGGCC-mediated neurodegeneration. There is a need for a peptide that mimics a Pur protein nucleic acid binding domain that may also act as a Pur agonist.

Another example of a repeat expansion disorder is Fragile X Syndrome (FXS). FXS is a condition that is genetically inherited as part of the X-chromosome and is most common in males. It is caused by a mutation in the FMR1 gene that creates more triplet repeats of CGG than normal. This repeat is a classic Pur binding element. Symptoms of FXS include different physical features, such as long face and large ears, intellectual disability, and behavioral problems, such as attention deficit disorder (ADD). As these expanded G-rich repeats have been studied more closely, it has been found that the Pur family of single-stranded or double-stranded nucleic acid-binding proteins interact with these repeats and possibly are sequestered away from their normal functions. There is a need for a peptide that can be used to bind to the G-rich repeats instead of Purα and Purβ, freeing up needed Pur proteins to proceed with their normal function.

BRIEF SUMMARY OF THE INVENTION

In one aspect, the present invention relates to synthetic peptides which are capable of binding to PUR elements. The invention also relates to the use of the peptides in the prevention or treatment of cancer, HIV, or nucleotide repeat diseases. In one aspect, the present invention provides a synthetic TZIP peptide comprising the amino acid sequence LASTFVTRDNKRYFMDLKENQRGRFMRVSQVG-TRGYRNSLTVSYSVAWLEFRTHLCKLIDEYA KLQYARAKRRQARRQIRQQQQQQEE (SEQ ID NO: 1).

In one aspect, the present invention provides a peptide comprising the amino acid sequence LASTFVTRDNKRYF-MDLKENQRGRFMRVSQVGTRGYRNSLTVSYS-VAWLEFRTHLCKLIDEYA KLQYARAKRRQ-ARRQIRQQQQQQEE (SEQ ID NO: 1) or a variant thereof.

In another aspect, the invention provides the amino acid sequence LASTFVTRDNKRYFMDLKENQRGRFM-RVSQVGTRGYRNSLTVSYSVAWLEFRTHLCKLIDEYA KLQYARAKRRQARRQIRQQQQQQEE (SEQ ID NO: 1).

In a still further aspect, the invention provides a method for modulating the proliferation of cells that comprises administering a therapeutically effective amount of a therapeutic agent comprising the amino acid sequence LAST-FVTRDNKRYFMDLKENQRGRFMRVSQVGTRGYRN-SLTVSYSVAWLEFRTHLCKLIDEYA KLQYARAKRRQARRQIRQQQQQQEE (SEQ ID NO: 1) and a pharmaceutically acceptable carrier.

In another aspect, the invention provides a method for treating a cancer in a subject that includes administering a therapeutically effective amount of a therapeutic agent comprising the amino acid sequence LASTFVTRDNKRYFM-DLKENQRGRFMRVSQVGTRGYRNSLTVSYSVAWLE-FRTHLCKLIDEYA KLQYARAKRRQARRQIRQQQQQQEE (SEQ ID NO: 1) and a pharmaceutically acceptable carrier, wherein the cancer is characterized as having amplified c-MYC genes.

In another aspect, the invention further provides a method for treating cancer in a subject, where the cancer is selected from the group consisting of small cell lung carcinoma, brain tumor, acute myelogenous leukemia (AML), malignant melanoma, mesothelioma, prostate, lymphoma, colon, bladder, and head and neck cancer.

In a further aspect, the method for treating a cancer in a subject comprises administering a therapeutically effective amount of a therapeutic agent having an amino acid sequence that
  (a) binds upstream of the c-MYC gene;
  (b) binds retinoblastoma protein; and
  (c) recruits cell cycle regulatory proteins to a DNA binding site of a cell to inhibit cell proliferation,
wherein the cancer is characterized as having amplified c-MYC genes.

In another aspect, the cancer is selected from the group consisting of small cell lung carcinoma, brain tumor, AML, malignant melanoma, mesothelioma, prostate, lymphoma, colon, bladder, and head and neck cancer.

In another aspect the agent used to treat cancer contains the amino acid sequence LASTFVTRDNKRYFMDLKEN-QRGRFMRVSQVGTRGYRNSLTVSYSVAWLEFRTHL-CKLIDEYA KLQYARAKRRQARRQIRQQQQQQEE (SEQ ID NO: 1).

In another aspect, the agent is soluble in aqueous solution.

In another aspect, the agent has an amino acid sequence comprising an enhanced cell transport sequence capable of allowing the agent entry into cancer cells from the bloodstream.

In another aspect, the agent does not significantly affect growth of noncancerous primary epithelial cells.

In another aspect the agent inhibits cancer cell proliferation.

In still another aspect, the invention is a method of treating HIV by administering a therapeutically effective amount of a peptide comprising the amino acid sequence LASTFVTRDNKRYFMDLKENQRGRFMRVSQVG-TRGYRNSLTVSYSVAWLEFRTHLCKLIDEYA KLQ-YARAKRRQARRQIRQQQQQQEE (SEQ ID NO: 1) or a variant thereof.

In another aspect of the invention the HIV resides in human cells.

In another aspect of the invention, the human cells are selected from the group consisting of blood cells and bone marrow cells.

In another aspect of the invention, the HIV resides in brain tissue.

In another aspect of the invention, the brain tissue is comprised of glial cells, neurons, astrocytes, or microglial cells.

In another aspect of the invention, nerve damage is prevented.

In another aspect of the invention, the nerve damage is in the peripheral nervous system.

In another aspect of the invention, the nerve damages is in the central nervous system.

In another aspect of the invention, a method of preventing HIV infection comprising administering a peptide comprising the amino acid sequence LASTFVTRDNKRYFMDLKENQRGRFMRVSQVGTRGYRNSLTVSYSVAWLEFRTHLCKLIDEYA KLQYARAKRRQARRQIRQQQQQQQEE (SEQ ID NO: 1) or a variant thereof, is provided.

In another aspect of the invention, the peptide is administered in a cream.

In another aspect of the invention, the cream is applied to the vaginal or anal region.

In another aspect of the invention, a method of treating an expanded nucleotide repeat disease by administering a peptide comprising the amino acid sequence LASTFVTRDNKRYFMDLKENQRGRFMRVSQVGTRGYRNSLTVSYSVAWLEFRTHLCKLIDEYA KLQYARAKRRQARRQIRQQQQQQQEE (SEQ ID NO: 1) or a variant thereof, is provided. Specific examples of expanded nucleotide repeat diseases that can be treated with the peptides disclosed herein include, but are not limited to, ALS and fragile X syndrome.

BRIEF DESCRIPTION OF THE DRAWINGS

FIG. 10 shows the amino acid sequences of Cyclin T1 (SEQ ID NO: 4), IRF7 (SEQ ID NO: 8) and examples of peptides of the present invention. TZIP disclosed as SEQ ID NO: 5, TZIP-M1 disclosed as SEQ ID NO: 9, TZIP-M2 disclosed as SEQ ID NO: 10 and TZIP-M3 disclosed as SEQ ID NO: 11.

FIG. 11 is the nucleotide sequence used to generate a peptide of the present invention (SEQ ID NO: 12). The synthetic nucleotide cloned and sequenced is highlighted in grey. Primers used for sequencing are double underlined.

FIG. 12 provides images of Coomassie Stains and Western Detection of Protein Purification for Purα (FIG. 12A) and Purβ (FIG. 12B).

FIG. 13A shows constant Purα with ALS ssDNA alone. FIG. 13B shows constant Purβ with ALS ssDNA alone. FIG. 13C shows constant TZIP with ALS ssDNA alone.

DETAILED DESCRIPTION OF THE INVENTION

Figure 1:
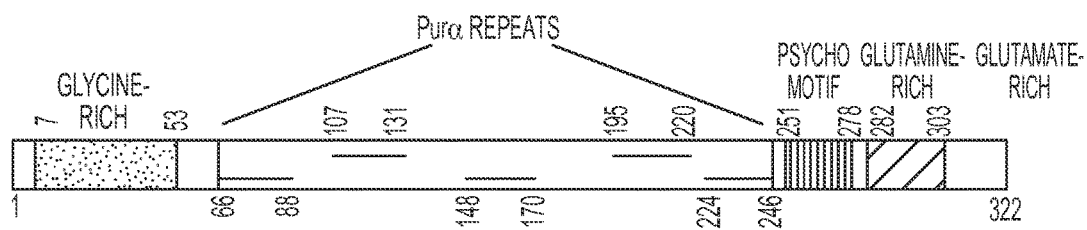
FIG. 1 is an image depicting the structural domains of the Purα protein.

The terms "treatment," "treating," "treat," "therapy," "therapeutic," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, may or may not be diagnosed as having it; (b) inhibiting the disease symptom, i.e., arresting its development; or (c) relieving the disease symptom, i.e., causing regression of the disease or symptom.

The term "pharmaceutically acceptable carrier," as used herein, refers to any and all solvents, dispersion media, coatings, antibacterial and antifungal agent, isotonic and absorption delaying agents for pharmaceutical active substances as are well known in the art. The term "pharmaceutical" or "agent", as used herein, includes biological pharmaceuticals such as proteins, peptides, and oligonucleotides. Except insofar as any conventional media or agent is incompatible with the agent, its use in the therapeutic pharmaceutical compositions is contemplated. Supplementary compounds or biological pharmaceuticals can also be incorporated into the pharmaceutical compositions.

As used herein, the term "excipient" refers to the additives used to convert a synthetic agent into a form suitable for its intended purpose. For pharmaceutical compositions of the present invention suitable for administration to a human, the term "excipient" includes those excipients described in the HANDBOOK OF PHARMACEUTICAL EXCIPIENTS, American Pharmaceutical Association, 2nd Ed. (1994), which is herein incorporated in its entirety. The term "excipients" is meant to include fillers, binders, disintegrating agents, lubricants, solvents, suspending agents, dyes, extenders, surfactants, auxiliaries and the like. Liquid excipients can be selected from various oils, including those of petroleum, animal, vegetable or synthetic origin, such as, peanut oil, soybean oil, mineral oil, sesame oil, hydrogenated vegetable oil, cottonseed oil, groundnut oils, corn oil, germ oil, olive oil, or castor oil, and so forth.

Suitable excipients also include, but are not limited to, fillers such as saccharides, lactose, fructose, sucrose, inositol, mannitol or sorbitol, xylitol, trehalose, cellulose preparations and/or calcium phosphates, tricalcium phosphate or calcium hydrogen phosphate, as well as starch paste, using modified starch, maize starch, wheat starch, rice starch, potato starch, gelatin, tragacanth, ethoxylated isostearyl alcohols, polyoxyethylene sorbitol and sorbitan esters, microcrystalline cellulose, hydroxypropyl cellulose, methyl cellulose, hydroxypropyl methyl cellulose, aluminum metahydroxide, bentonite, sodium carboxymethylcellulose, croscarmellose sodium, crospovidone and sodium starch glycolate, and/or polyvinyl pyrrolidine and mixtures thereof. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries include, silica, stearic acid or salts thereof, such as, magnesium stearate, sodium stearyl fumarate, or calcium stearate.

The expression "therapeutically effective amount" refers to an amount of an agent disclosed herein, that is effective for preventing, ameliorating, treating or delaying the onset of a disease or condition.

The pharmaceutical compositions of the inventions can be administered to any animal that can experience the beneficial effects of the agents of the invention. Such animals include humans and non-humans such as primates, pets and farm animals.

Pharmaceutical Compositions Comprising Agents of the Invention

The present invention also comprises pharmaceutical compositions comprising the agents disclosed herein. Routes of administration and dosages of effective amounts of the pharmaceutical compositions comprising the agents are also disclosed. The peptides of the present invention can be administered in combination with other pharmaceutical agents in a variety of protocols for effective treatment of disease.

The pharmaceutical compositions of the present invention are administered to a subject in a manner known in the art. The dosage administered will be dependent upon the age, health, and weight of the recipient, kind of concurrent treatment, if any, frequency of treatment, and the nature of the effect desired.

In addition to the agents disclosed herein, the pharmaceutical compositions of the present invention may further comprise at least one of any suitable auxiliaries including, but not limited to, diluents, binders, stabilizers, buffers, salts, lipophilic solvents, preservatives, adjuvants or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the agent.

Pharmaceutical excipients and additives useful in the present invention can also include, but are not limited to, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like.

Pharmaceutical compositions suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The pharmaceutical compositions may be presented in unit-dose or multi-dose containers, sealed ampules and vials, and may be stored in a freeze-dried (lyophilized) condition requiring only the addition of the sterile liquid carrier, water for injections, immediately prior to use. Extemporaneous injection solutions and suspensions may be prepared from sterile powders, granules and tablets of the kind previously described.

For parenteral administration, sterile suspensions and solutions are desired. Isotonic preparations which generally contain suitable preservatives are employed when intravenous administration is desired. The pharmaceutical compositions may be administered parenterally via injection of a pharmaceutical composition comprising an agent dissolved in an inert liquid carrier. The term "parenteral," as used herein, includes, but is not limited to, subcutaneous injections, intravenous, intramuscular, intraperitoneal injections, or infusion techniques. Acceptable liquid carriers include, vegetable oils such as peanut oil, cotton seed oil, sesame oil and the like, as well as organic solvents such as solketal, glycerol formal and the like. The pharmaceutical compositions may be prepared by dissolving or suspending the agent in the liquid carrier such that the final formulation contains from about 0.005% to 30% by weight of a agent.

The composition of the invention can also include additional therapeutic agents such as, but not limited to hydrophilic drugs, hydrophobic drugs, hydrophilic macromolecules, cytokines, peptidomimetics, peptides, proteins, toxoids, sera, antibodies, vaccines, nucleosides, nucleotides, nucleoside analogs, genetic materials and/or combinations thereof.

In addition to agents and pharmaceutical compositions of the invention, and additional pharmaceutically active agents, the pharmaceutical formulation can also contain suitable pharmaceutically acceptable carriers comprising excipients and auxiliaries that facilitate processing of the active agents into preparations that can be administered to animals, as described herein.

Pharmaceutical formulations useful in the present invention can contain a quantity of as agent(s) according to this invention in an amount effective to treat the condition, disorder or disease of the subject being treated.

The invention is also directed to a kit form useful for administration to patients in need thereof. The kit may have a carrier means being compartmentalized in close confinement to receive two or more container means therein, having a first container means containing a therapeutically effective amount of a pharmaceutical composition of the invention and a carrier, excipient or diluent. Optionally, the kit can have additional container mean(s) comprising a therapeutically effective amount of additional agents.

The kit comprises a container for the separate pharmaceutical compositions such as a divided bottle or a divided foil packet, however, the separate pharmaceutical compositions can also be contained within a single, undivided container. Typically, the kit contains directions for administration of the separate components. The kit form is particularly advantageous when the separate components are preferably administered at different dosage intervals, or when titration of the individual components of the combination is desired by the prescribing physician. The kits of the invention include testing and screening kits and methods, to enable practitioners to measure levels of the active ingredients in bodily fluids. The kits of the invention also include research-grade reagents and kits available for use and purchase by research entities.

Routes of Administration of Pharmaceutical Compositions Comprising the Agents of the Invention The invention further relates to the administration of at least one agent disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarenal, intraretinal, intraspinal, intrasynovial, intrathoracic, intrauterine, intravesical, bolus, vaginal, rectal, buccal, sublingual, intranasal, iontophoretic means, or transdermal means.

Methods of Preparation of Pharmaceutical Compositions of the Present Invention

Methods of preparing various pharmaceutical compositions with a certain amount of active ingredients are known, or will be apparent in light of this disclosure, to those skilled in the art. Methods of preparing said pharmaceutical compositions can incorporate other suitable pharmaceutical excipients and their formulations as described in Remington's Pharmaceutical Sciences, Martin, E. W., ed., Mack Publishing Company, 19th ed. (1995).

One of ordinary skill in the art will appreciate that a method of administering pharmaceutically effective amounts of the pharmaceutical compositions of the invention to a patient in need thereof, can be determined empirically, or by standards currently recognized in the medical arts. The agents can be administered to a patient as pharmaceutical compositions in combination with one or more pharmaceutically acceptable excipients. It will be understood that, when administered to a human patient, the total daily usage of the agents of the pharmaceutical compositions of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, gender and diet of the patient; the time of administration, route of administration, and rate of excretion of the agent; the duration of the treatment; drugs used in combination or coincidental with the specific agent; and like factors well known in the medical arts. It is well within the skill of the art to start doses of the agents at levels lower than those required to achieve the desired therapeutic effect and to gradually increase the dosages until the desired effect is achieved.

Dosaging can also be administered in a patient-specific manner to provide a predetermined concentration of the agents in the blood, as determined by techniques accepted and routine in the art.

Dosage Determinations

In general, the agents disclosed herein may be used alone or in concert with other therapeutic agents at appropriate dosages defined by routine testing in order to obtain optimal efficacy while minimizing any potential toxicity. The dosage regimen utilizing an agent of the present invention may be selected in accordance with a variety of factors including type, species, age, weight, sex, medical condition of the patient; the severity of the condition to be treated; the route of administration; the renal and hepatic function of the patient; and the particular agent employed. A physician or veterinarian of ordinary skill can readily determine and prescribe the effective amount of the drug required to prevent, counter, or arrest the progress of the condition.

Pur Agonists

The "TZIP" peptide disclosed herein is a novel synthetic Purα agonist peptide that exhibits anti-cancer activity. TZIP is a generic Pur repeat that possesses characteristics of all Pur family members. It reverses deregulated cell growth and can be effective in treating various cancers, including small cell lung carcinoma, prostate cancer, lymphoma, brain tumors, colon cancer, bladder cancer, AML, malignant melanoma, mesothelioma, and cancers of the head and neck.

When used in therapy, the TZIP peptide is designed to modulate the growth of cancer cells by binding to c-MYC genes of these cells to prevent unchecked progression of the cell cycle. Specifically, the TZIP peptide is designed to bind to a sequence upstream of the c-MYC gene to activate a tumor suppressor pathway that causes cancer cells to undergo apoptosis. Moreover, the TZIP peptide is designed to maximize recruitment of cell cycle regulatory proteins to its DNA binding sites to normalize the control of cancer cell proliferation. Remarkably, the TZIP peptide does not have any significant effect on the growth of normal, primary epithelial cells.

The TZIP peptide can be used to treat or prevent SCLC, prostate cancer, cancers of the colon, head and neck, bladder cancer, mesothelioma, lymphoma, various brain tumors, AML, malignant melanomas, and other tumors and cancers with amplified c-MYC genes.

The TZIP peptide is a novel Purα agonist that contains sequences that bind DNA via Pur elements and protein-protein interacting domains. The mimetic peptide contains sequences associated with activities of the Purα protein. The structural domains of the Purα protein are shown in FIG. 1. The TZIP peptide has the advantage of an incorporated, enhanced cell transport sequence of YARAKRRQARRQIR (SEQ ID NO: 2), which allows the TZIP peptide to access all cells, including cancer cells, and cells from the bloodstream. The polypeptide disclosed herein is particularly useful when formulated as a cream, such as a cosmetic cream because of the presence of the enhanced cell transport sequence in the peptide which facilitates transport of the peptide into the target cells.

The TZIP peptide was designed to optimize versions of protein motifs found throughout evolution to allow it to be effective in any animal. Peptide treatments frequently encounter an immune response as a toxic or ablating side effect. The TZIP peptide incorporates features that are in proteins normally secreted in humans and are thus unlikely to be highly immunogenic. In addition, the TZIP peptide works at such low concentrations and with such rapidity that an effective antitumor response may be achieved before any adaptive immune response is mounted.

The TZIP peptide can be administered as a pharmaceutical composition to treat or prevent cancers, especially cancers that exhibit amplified c-MYC genes. In a preferred embodiment, a pharmaceutical composition comprises at least one peptide comprising the amino acid sequence of the TZIP peptide: LASTFVTRDNKRYFMDLKENQRGRFM-RVSQVGTRGYRNSLTVSYSVAWLEFRTHLCKLIDEYA KLQYARAKRRQARRQIRQQQQQQQEE (SEQ ID NO: 1) or a variant amino acid sequence, and a pharmaceutically acceptable carrier. A variant amino acid sequence ("TZIP variant") of the given TZIP amino acid sequence is a sequence with the side chains of, for example, one or more altered amino acid residues (for example, the amino acid residues are replaced with the side chain of another amino acid residue or some other side chain) such that the peptide is still able to bind to its Pur element in substantially the same way as a peptide consisting of the given amino acid sequence. For example, a peptide may be modified so that it maintains or improves the ability to interact with and bind a suitable Pur element to modulate cell proliferation. Moreover, those amino acid residues that are not essential to interact with the Pur element can be modified by replacement with another amino acid whose incorporation does not substantially affect the peptide's ability to behave as a Purα agonist and does not eliminate binding to the relevant Pur element. Thus, apart from the specifications given, the peptide of the invention may be any protein or peptide (including oligopeptides or polypeptides) that includes the amino acid sequences, or portion or variants thereof, as disclosed.

The design features of the TZIP peptide and TZIP variants are as follows:
1. It contains an amino acid motif optimized to bind to a sequence upstream of the c-MYC gene, a known oncogene that participates in the progression of SCLC.
2. It contains a motif optimized to bind a protein (Rb) that activates a tumor suppressor pathway, thus steering cancer cells toward programmed cell death.
3. It contains an amino acid motif optimized to transport the peptide in and out of cells, thus allowing it to gain access to cancer cells from the bloodstream.
4. It contains a motif designed to maximize recruitment of cell cycle regulatory proteins to its DNA binding sites in order to normalize the control of cancer cell proliferation.
5. It has been designed for maximum solubility in aqueous solutions, thus allowing it to be administered in non-toxic media.

The TZIP peptide and TZIP variants are designed to behave as Purα agonists by recruiting Purα interacting proteins to inhibit cell proliferation. To carry out functions within the cell, the TZIP peptide and TZIP variants are designed to tightly bind to their PUR element. These PUR elements are found within the promoters of genes such as the well characterized Purα target, c-MYC, the protein product of which modulates cell cycle progression. The TZIP peptide and TZIP variants are designed to effectively recruit partner proteins to their PUR DNA-binding element, where Purα binds with high affinity and locally strand separates DNA.

The TZIP peptide and TZIP variants are designed to inhibit S phase progression and cell growth in abnormal cells (e.g. cancer cells) when introduced in G1 phase of the cell cycle. It is intended that cell cycle progression is modulated when the TZIP peptide and TZIP variants enter the cell nucleus and cytoplasm to directly bind to Rb protein in G1 phase, and will be released when Rb becomes phosphorylated. Rb activates tumor suppressor pathways to steer cancer cells toward programmed cell death. The TZIP peptide and TZIP variants are also intended to bind Cdk4 to regulate cell proliferation.

The TZIP Peptide is a Therapeutic Agent

The therapeutic peptides of the present invention are based on a generic Pur protein nucleic acid binding repeat and incorporate amino acids that facilitate their use in therapy. The proteins are designed to alter the biological pathways of cells, both normal and abnormal, in mammals.

The TZIP peptide (and TZIP variants) can be administered as therapeutic agents for prevention, prophylaxis, or other therapy of cancerous diseases, such as diseases that exhibit amplified c-MYC genes. The TZIP peptide incorporates an enhanced cell transport sequence to allow it to enter cells efficiently. The TZIP peptide can be administered intravesicularly to avoid systemic delivery methods that require higher dosages. The TZIP peptide (and TZIP variants) can be transfected or co-transfected into cells with a vector, or coupled with monoclonal antibodies for specific tumor types. The TZIP peptide (and TZIP variants) can also be microinjected into cells at certain phases to arrest cell-cycle progression. Moreover, the TZIP peptide (and TZIP variants) can be adapted for administration by any appropriate route, for example by the oral, nasal, topical (including buccal, sublingual, or transdermal), or parenteral (including subcutaneous, intracutaneous, intramuscular, intraarticular, intraperitoneal, intrasynovial, intrasternal, intrathecal, intralesional, intravenous, or intradermal injections or infusions) route. For human administration, the formulations preferably meet sterility, pyrogenicity, general safety, and purity as required by FDA Office and Biologics standards.

Dosage amounts of and modifications to the TZIP peptide (and TZIP variants) may be tissue, cancer, and/or patient specific. For example, the exact dosage amount of and/or modification to the TZIP peptide (and TZIP variants) can be guided by expression patterns of the peptide in a given tissue to avoid side effects or to enhance therapeutic effect. The selection of a dosage amount or modification of the peptide may be dependent upon the specific type of cancer sought to be treated, or the stage of the disease. The selected dosage amount is a therapeutically effective amount, or an amount sufficient to retard or arrest growth of cancerous cells. The effect of a certain amount of the pharmaceutical composition can be monitored by observing the growth of the tumor treated or its recurrence. Determining a therapeutically effective amount is well within the skill of a practicing physician. Accordingly, it may be necessary for the therapist to titer the dosage and modify the route of administration as required to obtain the maximal therapeutic effect.

The TZIP peptide (and TZIP variants) can be used to treat or prevent SCLC, prostate cancer, cancers of the colon, head and neck, bladder cancer, mesothelioma, lymphoma, various brain tumors, bladder cancer, AML, malignant melanoma, and other tumors and cancers with amplified c-MYC genes.

Tat Agonists

Synthetic peptide agents mimicking a structural motif common to Tat binding partners Cyclin T1, Purα and IRFs 3 and 7 can be used to assess the ability of a Tat-binding amino acid motif present in cellular partner proteins to serve as a target for interference with Tat co-opting of cellular functions. These peptide agents can be tested for their ability to abrogate transactivation of HIV-1 transcription by Tat and to interfere with Tat effects on IRF3 and 7 relocalization in neural cells.

Figure 9A:
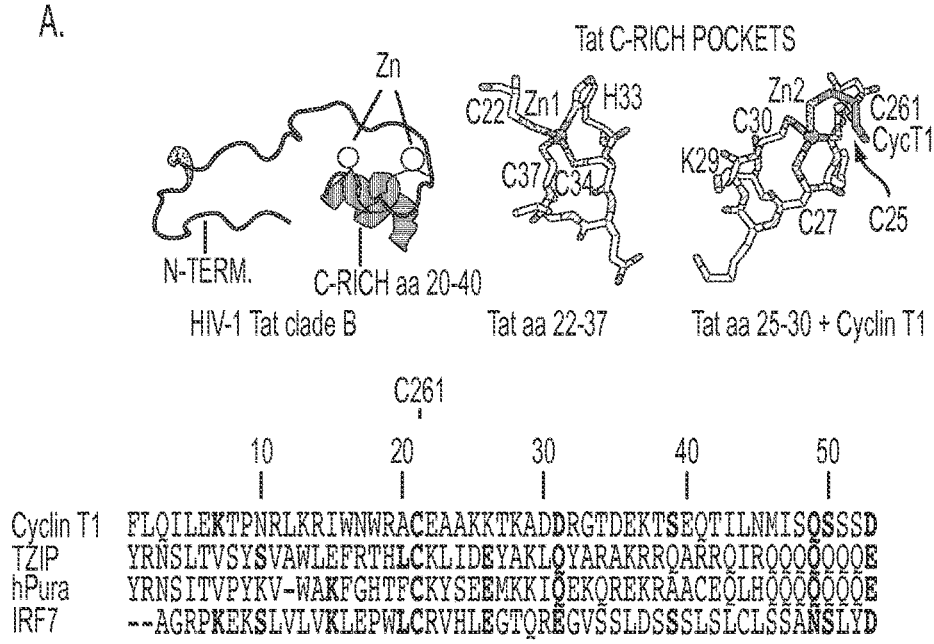
FIG. 9A shows the crystal structures of a portion of Tat alone, a portion of Tat bound to cyclin T1 and HIV-1 Tat clade B as well as the amino acid sequences of cyclin T1 (SEQ ID NO: 4), TZIP (SEQ ID NO: 5), Purα A (SEQ ID NO: 6) and IRF7 (SEQ ID NO: 7).

As is shown in FIG. 9A, mutation of either Tat C22 or C27 abolishes Tat transactivation. Two Zn ions are coordinated by two Tat C-rich domains within amino acids 20-38. Further, Cyclin T1 C261 participates in the binding to Zn2. This alters and stabilizes the folding of Tat, increasing its ability to bind the U-rich bulge in TAR RNA and to bind to Cyclin T1/Cdk9. Mutation of Tat C22 also abrogates binding to Purα. Purα and IRFs 3, 7 also have a potential Zn-binding region with structural features similar to those of Cyclin T1, as shown for IRF7 in FIG. 9A. Therefore, a peptide with features resembling those of the region of C261 of Cyclin T1 would bind the Zn2 C-rich domain and disrupt Tat activities. This peptide has been synthesized and is shown in Figure in order to minimize potential side effects in vivo. A basic transporter sequence, YARAKRRQARRQIR (SEQ ID NO: 2), was also incorporated into the TZIP peptide. This transporter sequence allows the polypeptide to enter cells.

HIV Treatment and Prevention

The TZIP peptide (and TZIP variants) of the present invention can also be used to treat HIV infection. Specifically, the peptides can be used to treat HIV-infected cells. These peptides can be taken up by the infected cells and stop the transactivation of HIV-1 transcription. Further, the peptides of the present invention may be incorporated into various prophylactic applications that will prevent the transmission of HIV. For example, a peptide of the invention can be incorporated into a topical treatment that can be applied to the penile, vaginal, or anal region in order to prevent transmission. The peptides can also be incorporated into various birth control devices (e.g. male and female condoms, diaphragms, cervical caps and cervical shields) and/or lubricants used with these devices or lubricants used without these devices.

Nucleotide Repeat Diseases

The TZIP peptide (and TZIP variants) can also be used to treat nucleotide repeat diseases. More specifically, introducing the TZIP peptide (or TZIP variants) to an affected cell can displace a bound Pur protein, thereby preventing sequestration-related cellular damage. Therefore, overexpression of these Pur proteins could cancel out or lessen developmental and intellectual disabilities that are caused by the expanded G-rich repeats. These Pur proteins include Purα, Purβ, and Purγ. The TZIP peptide can modify the binding of Pur proteins to this expanded repeat. TZIP functions cooperatively at less than 1 µM with Purα to enhance binding to the GGGGCC repeat expanded and implicated in ALS. If Pur proteins are indeed sequestered away, then TZIP can be used to bind to the G-rich repeats instead of Purα, Purβ or Purγ, freeing up needed Pur proteins to proceed with their normal function.

EXAMPLES

The following examples are presented for the purpose of illustration only and are not intended to be limiting.

Example 1

Figure 2:
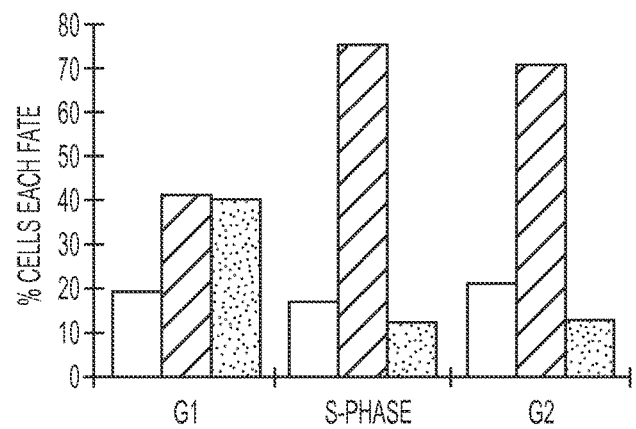
FIG. 2 is a graph which shows the effect on cell fate when Purα is microinjected into NIH3T3 cells at various cell-cycle positions.

Purα was injected into NIH3T3 cells during various cell-cycle transition points to determine the effects of elevated Purα levels at different phases of the cell cycle. The introduction of Purα in $G_1$ phase arrested cells at the $G_1$-S boundary, causing programmed cell death (see FIG. 2). In FIG. 2, the clear bar represents dividing cells, the black bar represents non-dividing cells, and the shaded bar represents rapid cell death. Introduction of Purα in later phases, such as $G_2$-M phase, arrested, but did not prevent, complete replication of the genome.

Example 2

Expression of Purα was shown to block proliferation of a variety of oncologically transformed cells. Cells were released from a double thymidine block, which arrests cells upon entry to S phase, into normal growth medium. Samples were subjected to fluorescence-activated cell sorting to determine cellular DNA content.

Figure 3:
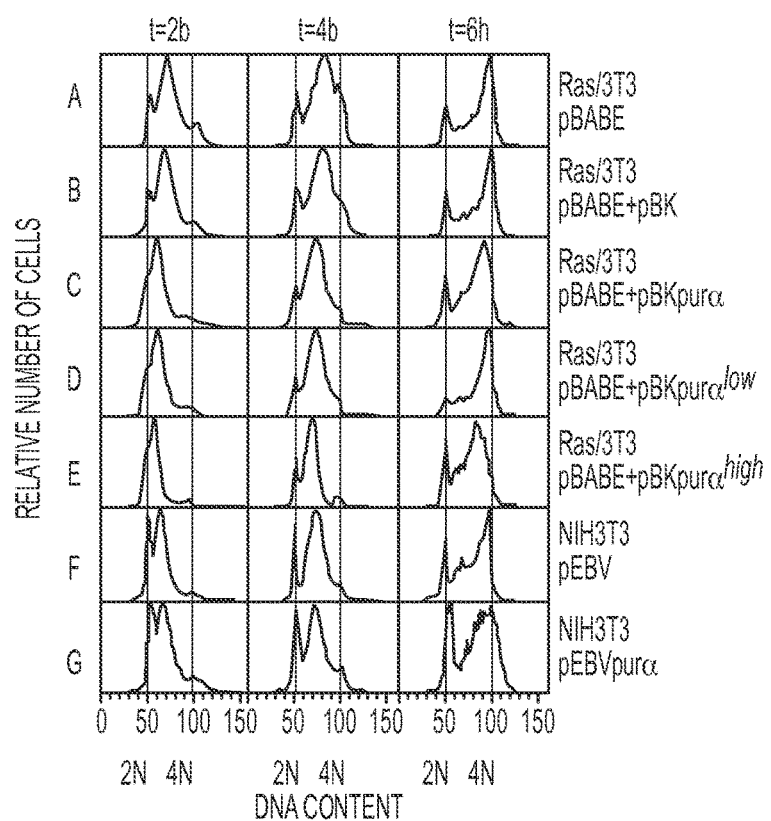
FIG. 3 is a graph which shows that Purα retards entry into S phase and progression through S phase in ras-transformed cells.

Two to five-fold elevated levels of Purα in stably transfected cell lines retarded entry into and progression through S phase in both ras-transformed and non-transformed cells. FIG. 3 shows the dose-dependent action of Purα to inhibit cell cycle progression in ras-transformed and non-transformed NIH3T3 cells transfected to over-express Purα. Stably transfected or co-transfected pools and transfected clones are shown on the right.

A pool of ras-transformed cells were stably transfected or co-transfected with the following: (a) pBABE, an empty vector; (b) pBABE+pBK, both empty expression vectors; (c) pBABE+pBKPurα, to over-express Purα; (d) pBABE+pBKPurα$^{low}$ to express Purα at a level near that of endogenous Purα; (e) pBABE+pBKPurα$^{high}$ to express Purα at a level nearly 5-fold that of endogenous Purα; (f) pEBV, an empty expression vector (g) pEBVPurα to over-express Purα. 4N indicates completion of DNA synthesis.

The lower levels of Purα in the stably transfected lines did not fully arrest the cycle, but significantly retarded the progression of the cycle at the same point. Referring to FIG. 3, comparison of rows c through e with row b show that expression of Purα retarded both entry into S-phase and progression through S-phase in the ras-transformed cells. Thus, Purα was shown to retard progression through S phase in a dose-dependent manner.

Figure 4:
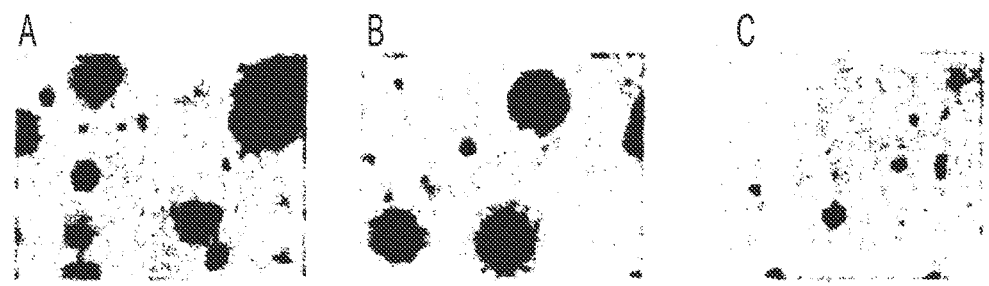
FIG. 4 is an image which shows the effect of Purα on anchorage independent growth of ras-transformed NIH3T3 cells.

Purα also antagonizes colony formation and anchorage-independent growth related to ras-transformation of NIH3T3 cells. Ras-transformed cells were transfected with pBABE (empty vector) and either pBK (empty vector) or pBKPurα expression construct and selected for puromycin resistance. Referring to FIG. 4, panel A (pBABE) and panel B (pBABE+pBK) show anchorage independent cell growth. Panel C (pBABE and pBKPurα), however, shows that Purα repressed anchorage independent growth.

Example 3

Purα was shown to bind the hypophosphorylated form of Rb, p110$^{RB}$. Rb was detected in extracts of monkey CV-1 cells complexed with Purα. These complexes can be immunoextracted from cell lysates using monoclonal antibodies to either Purα or Rb.

Proteins expressed in bacteria were bound to glutathione-agarose beads. Unfused GST was prepared in the same manner for use as a control. Beads containing equivalent amounts of each protein were used for each lane. Beads were collected, washed, and bound proteins were subjected to electrophoresis. The proteins were then blotted and probed with anti-Rb monoclonal antibody.

Figure 5:
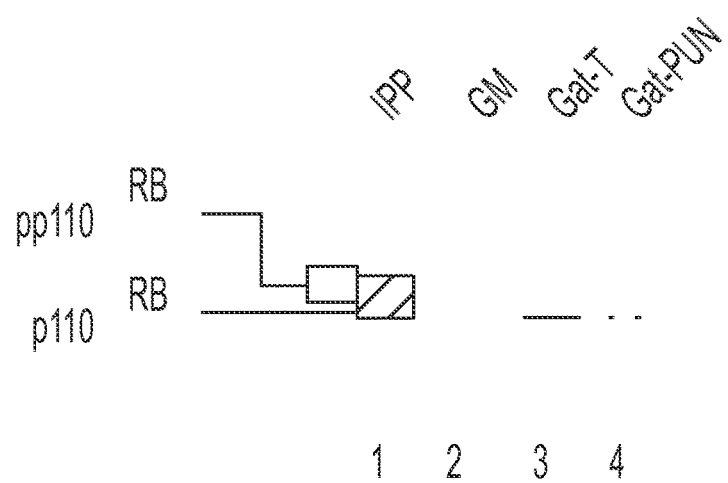
FIG. 5 is an image showing that Purα binds $p110^{RB}$, the hypophosphorylated form of Rb.

FIG. 5 shows that both Gst-Purα and Gst-T (+control, a mutant form of SV40 large T-antigen) bind exclusively to the hypophosphorylated forms of p110$^{RB}$. In contrast, binding of Rb to control GST alone was nil. IPP represents Rb immunoprecipitated from WR2E3 cells using rabbit polyclonal anti-Rb antibody. In proliferating cells, the Rb protein existed in several states of phosphorylation, the hypophosphorylated state, p110$^{RB}$, migrating more rapidly on SDS gels (lane 1).

Example 4

The TZIP peptide was shown to inhibit growth of SCLC cells in low concentrations. The peptide was tested against SCLC cells in culture. The cell lines included H82, H146, and controls. The H82 cell line has amplified c-MYC genes and H146 has increased levels of expression of c-MYC. The controls were normal epithelial cells and HeLa cells (a cervical cancer cell line with no known changes in c-MYC).

Figure 6:
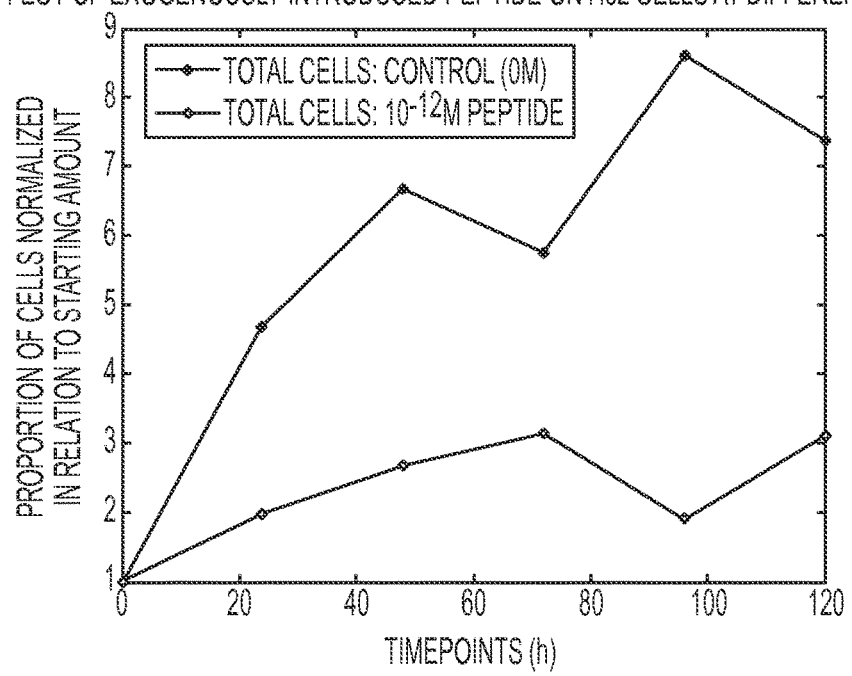
FIG. 6 is a graph which shows the effect of exogenously introduced TZIP peptide on cell counts of H82 cells at various times.

H82 SCLC cells were grown in suspension in small cell culture wells in RPMI medium with 10% fetal bovine serum. At time 0, the TZIP peptide was added to the medium at a final concentration of $10^{-12}$ M. Control cells received no peptide. The TZIP peptide was added as a stock solution of 200 µg in 200 µL of deionized water. Time points were taken as shown in FIG. 6, and cells were counted using a hemocytometer. As shown in FIG. 6, inhibitory effects of the peptide were evident at one day post treatment and no further growth of the treated cancer cells was evident after three days.

Figure 7:
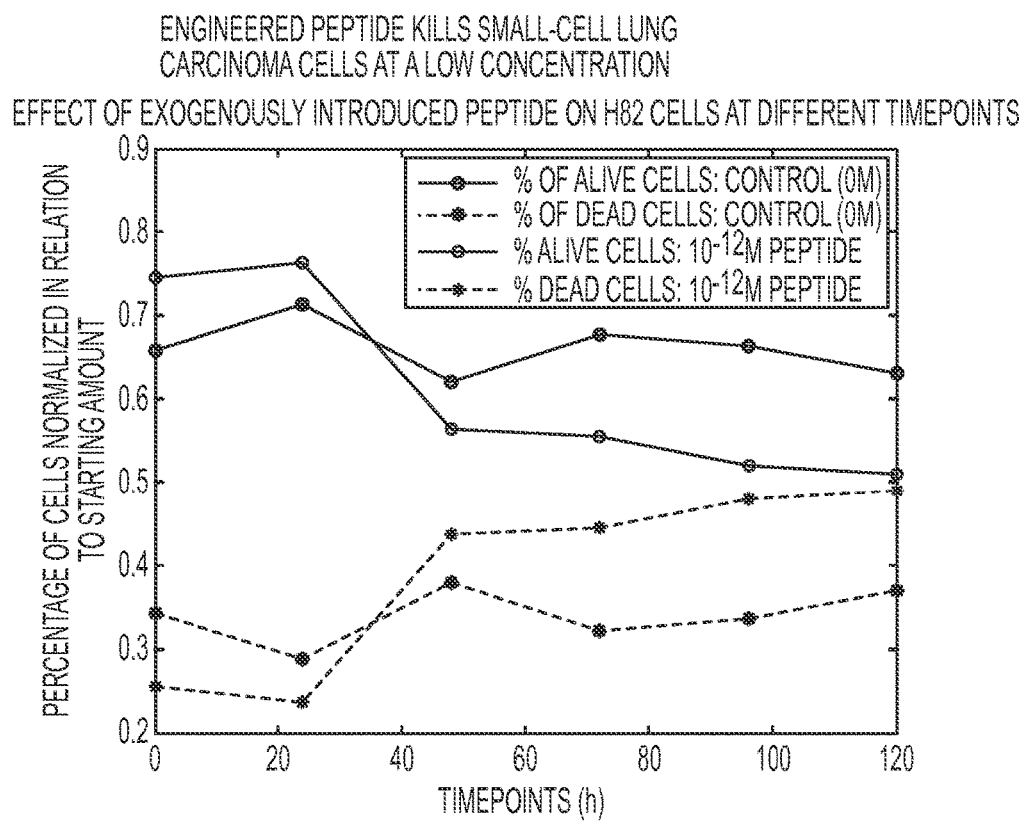
FIG. 7 is a graph which shows the effects of exogenously introduced TZIP peptide on treated and untreated H82 cells measured using dye trypan blue.

Referring to FIG. 7, a subset of H82 cells was treated with the TZIP peptide and the dye trypan blue, which is excluded from live cells. The H82 cells were otherwise treated as previously described and H82 cells used as a control were untreated. The percentages of living cells are represented by solid lines, and the percentages of dead cells are represented by dotted lines. The TZIP peptide killed TZIP-treated H82 cells. In contrast, there were very slight changes over time in percentages of either living or dead cells in the untreated controls.

Example 5

Figure 8:
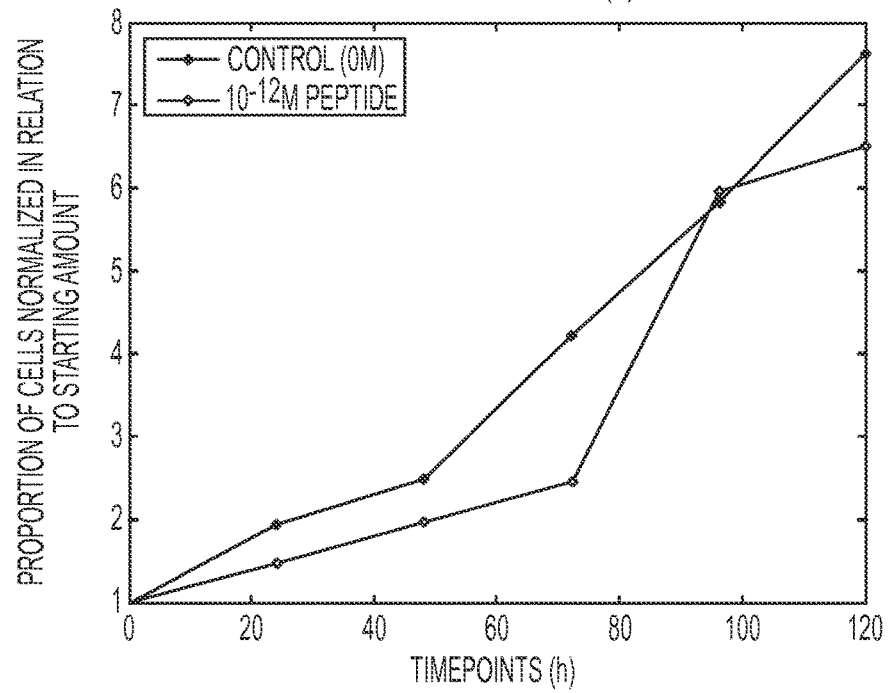
FIG. 8 is a graph which shows the effect of exogenously introduced TZIP peptide on HeLa(A) cells.

The TZIP peptide was shown to have a minor effect on the growth of cervical cancer cell line HeLa. This was expected based on the lack of changes in c-MYC in HeLa cell lines. HeLa cells were grown in suspension and either treated or untreated with the TZIP peptide as described above for the H82 cells. Points were taken at different times post treatment, and cells were counted using a hemocytometer. As shown in FIG. 8, the TZIP peptide had little effect on the growth of HeLa cells compared to the significant effect the TZIP peptide had on SCLC cells. This difference was expected, as HeLa cells differ from SCLC cells in many aspects of tumor suppressor gene products and presence of oncogenes.

Other SCLC cell lines, human prostate cancer cell lines, human mesothelioma cells, and normal human epithelial cells have been treated with the TZIP peptide, and SCLC cells consistently showed the greatest inhibitory effects by the peptide. The TZIP peptide has been shown effective at inhibiting growth of prostate cancer cells while normal epithelial cells did not show any significant effects of treatment with the TZIP peptide.

Example 6

Figure 9B:
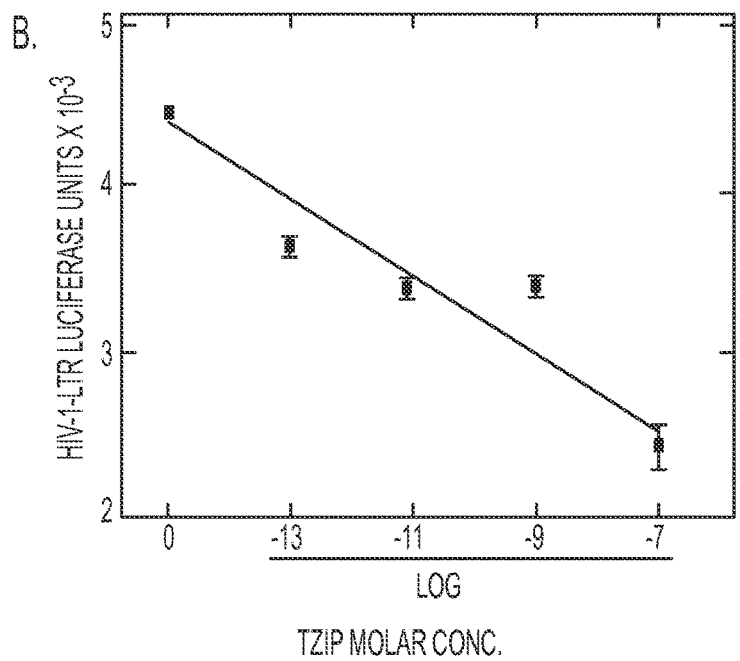
FIG. 9B is a graph which shows the inhibition of Tat transactivation in U-87 MG cells at different concentrations of the TZIP peptide.

The TZIP peptide's effect on Tat's ability to transactivate the HIV-1 LTR was tested. The results are shown in FIG. 9B. In this experiment, U-87 MG cells were transfected with the clade B HIV-1 LTR coupled to luciferase. They were also transfected to express Tat, clade B. In the absence of Tat transfection there is no luciferase activity. In the presence of the TZIP peptide, transactivation is inhibited over a broad range of low concentrations of the peptide added exogenously to the medium. The TZIP peptide did not display any effects on growth kinetics or morphology of U-87 MG or KG-1C cells. The results in FIG. 9B document inhibition of the HIV-1 LTR at low concentrations of peptide, levels which would be acceptable in humans.

Further inhibitors based on the initial TZIP model could target both HIV-1 and transcriptional activities and the ability of Tat to co-opt IRF3 and 7 responses. Experiments can be extended to transfected primary microglial cells. Microglial cells can be transfected to express Tat and the HIV-1 LTR-luciferase reporter as described above. Exogenous TZIP or an analog (FIG. 10) can be added at $10^{-14}$ to $10^{-7}$M and luciferase activity directed from the HIV-1 promoter assayed as in FIG. 9B. Results will assess the ability of synthetic peptides of the invention to modulate Tat interactions with critical partner proteins in microglial cells. Controls will be random peptides and analogs devised to have minimal effects. Once peptide sequences are optimized for inhibition of Tat activity, additional examples can be run on the peptides of the present invention that will examine their effects on HIV-1 microglial infection, and peptidomimetics can be designed to enhance treatment prospects.

Example 7

Figure 10:
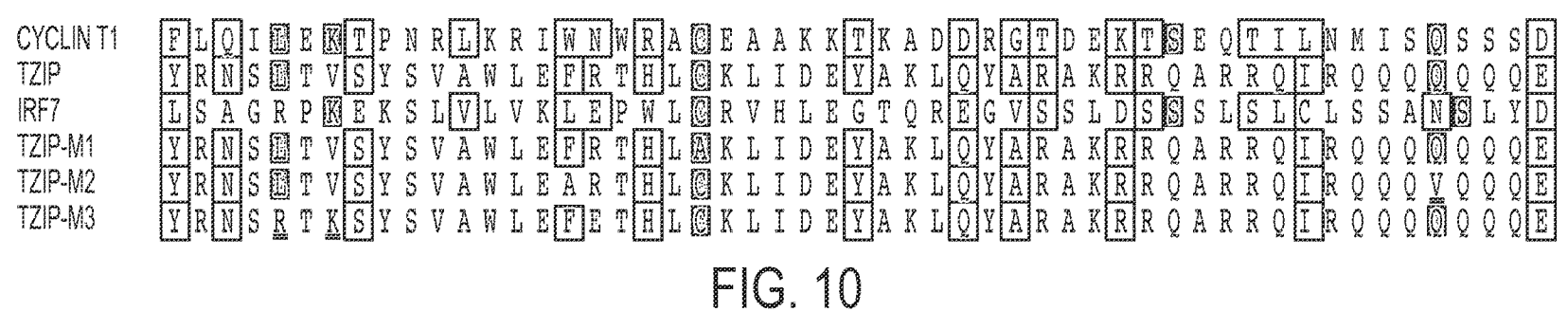

A transactivation assay can be used as an initial screen in generating more peptides based on the sequence and structure of the TZIP peptide. For example, additional peptides of the present invention (TZIP variants) have been synthesized and cloned as shown in FIG. 10. These clones can be tested in the assay used to generate FIG. 9B, which will measure each peptide's ability to inhibit Tat transactivation. The control will be cells not containing Tat and cells with luciferase expressed under direction of the irrelevant CAGGS promoters. The assay is improved by using exogenously added, purified Tat, which shows transactivation at $10^{-12}$ to $10^{-9}$ M. This allows for more direct control over Tat concentration.

IRFs 3 and 7 can also be examined using the transactivation assay based on FIG. 9B. It is believed that Tat activates the IRFs in glial cells, and that this activation will be inhibited by the TZIP peptide and other peptides of the present invention. U-87 MG cells can be transfected with Tat and several mutants thereof to obtain different levels of Tat activity. Wortman, M. J., Krachmarov, C. P., Kim, J. H., Gordon, R. G., Chepenik, L. G., Brady, J. N., Gallia, G. L., Khalili, K. and Johnson, E. M (2000). Interaction of HIV-1 Tat with Purα in nuclei of human glial cells: characterization of RNA-mediated protein-protein binding. J. Cell. Biochem., 77, 65-74. The levels of phosphorylation of IRFs 3 and 7 by immunoblotting can then be determined. This will quantify an important aspect of IRF 3 and 7 activation. This set of experiments can then be repeated in the presence of the TZIP peptide or TZIP variants and parameters of inhibition kinetics plotted and compared with those in the absence of such peptides. Information obtained will link activation of IRFs to the ability of Tat to bind partner proteins through its Zn2 pocket.

Example 8

To determine the molecular manner in which the peptides of the present invention inhibit the interaction of Tat with its partner proteins, a number of mutants of the TZIP peptide (TZIP variants) have been identified as shown in FIG. 10. Grey shading indicates identity with Cyclin T1, boxed amino acids indicate similarity to Cyclin T1 and double underlining indicates cloned mutants based on a TZIP coding sequence. It has been well-documented that Tat with N-terminal GST will pull down Cyclin T1 and Purα. Therefore, assays testing the peptides of the invention can be done as pull-downs using glutathione-agarose beads. Initially, GST-Tat can be added at equimolar concentrations to Cyclin T1 in the presence or absence of a peptide inhibitor at various concentrations. The amount of protein pulled down by GST-Tat can be quantified by immunoblotting. The $K_I$ and binding parameters of the peptide can be determined by standard methods. Mutating the peptides will yield valuable information regarding the contribution of each amino acid to the protein-protein binding involving the Cyclin T1-like domain. Ultimately, the information gained can help in the design of peptidomimetics inhibiting protein binding to that region.

Example 9

A DNA segment that comprises a 258 bp coding sequence for the synthetic peptide, TZIP, has been cloned. It is coupled to a 3' hexa-His sequence (SEQ ID NO: 3), for purification purposes and a 5' FLAG sequence, for antibody detection. The nucleotide sequence synthesized and cloned is shown in FIG. 11. This nucleotide coding sequence was designed to incorporate several unique features that enhance therapeutic aspects of the invention. Importantly, prior to the work of the present invention, there was no pre-existing natural coding sequence. The coding sequence in FIG. 11, therefore, is novel. As shown in FIG. 11, the peptide coding sequence for 89 amino acids ("aa"), flanked by EcoR1 and Pme1 restriction cleavage elements, is shown in grey. The cloned segment comprises 293 base pairs. Primer sequences used for sequencing are double underlined. The remaining sequences are from bacterial plasmid vector pIDTSMART (obtained commercially from Integrated DNA Technologies). The grey coding sequence was excised and ligated into mammalian expression vector pcDNA3.1-zeo (obtained commercially from Invitrogen Life Technologies), so that it possesses an amino terminal FLAG amino acid sequence for antibody recognition. This was accomplished by researching codon usage patterns from several different organisms, including humans and E. coli bacteria. In order to propagate the peptides of the present invention in large amount by using E. coli bacteria, but also use the peptides in human cells, the coding sequence was specifically designed so that it would work efficiently in both organisms. Further, the coding sequence was designed to use codons that can be easily mutated to generate point mutations of amino acids. This ability to create point mutations allows the person of skill in the art to easily make any analog of the peptides of the present invention, such that therapeutic value can be optimized. This is done by previously used molecular biological procedures employing polymerase chain reaction (PCR) to generate altered DNA sequences that can be cloned into the peptide coding sequence to propagate multiple copies, in bacteria, of a novel reading frame that will encode a mutated version of the peptide. The ability to rapidly mutate a peptide of the present invention allows the person of ordinary skill to make smaller optimal versions of the peptides of the invention and allows for the ability to perform peptidomimetics. Several mutants/variants generated using the method above are shown in FIG. 10. The present invention also encompasses any nucleotide sequence that encodes for the TZIP peptide (or TZIP variants).

Example 10

E. Coli bacteria were transformed with a GST-PURA expression construct, grown in LB-amp media, and induced with 0.1 mM IPTG. The process was repeated with the GST-PURB gene. Cell lysates from bacterial inductions were passed through the GSTrap Protein Purification module for Purα, and the GST Microspin Purification module for Purβ. SDS-PAGE-Lysates and elutions from isolation of GST-tagged Purα and Purβ were subjected to gel electrophoresis using an 8% polyacrylamide gel and Coomassie stained. Eluted fraction of the GST-tagged protein was dialyzed in 3 L 1×PBS for 3 hours. The eluted fraction was then adjusted to RNAse buffer (Johnson, Edward M, Daniel, Dianne C, and Gordon, Jennifer (2013) The Pur Protein Family: Genetic and Structural Features in Development and Disease. Journal of Cellular Physiology, vol 228 (930-937), which is incorporated by reference herein in its entirety). The solution was treated with 1×RNAse, then put through the GSTrap purification column again to remove the RNAse (Microspin Purification column for Purβ).

Elutions from RNAse treatment (Purα) and pre-RNAse treated elution (Purβ) were subjected to 8% polyacrylamide gel electrophoresis and transferred to a membrane using powdered milk in TBS-T. The Purα membrane was treated with a mouse monoclonal antibody (clone 10B12) against Purα developed in the Johnson laboratory. The Purβ membrane was treated with polyclonal rabbit anti-Purβ (Abcam). A secondary antibody treatment was performed, and the membrane was imaged using an autoradiography cassette to detect chemiluminescence.

Infrared oligonucleotides representing a GGGGCC hexanucleotide repeat expanded at C9ORF72 in ALS patients were custom ordered and are referred to as ALS ssDNA. 4% polyacrylamide gel electrophoresis was performed using IR-labeled oligonucleotides and imaged using the Li-Cor Odyssey IR imaging instrumentation and software.

Electrophoretic Mobility Shift Assay-Various combinations of Purα, Purβ, TZIP, and IR-labeled oligonucleotides were prepared in the 5× Johnson binding buffer (Bergemann, Andrew D and Johnson, Edward M (1992), The HeLa Pur Factor Binds Single-Stranded DNA at a Specific Element Conserved in Gene Flanking Regions and Origins of DNA Replication. Molecular and Cellular Biology, vol 12:3 (1257-1265), incorporated by reference herein in its entirety), adjusted to 5 mM DTT, 5 mM EDTA, and 0.5% Tween 20. 4% polyacrylamide gel electrophoresis was performed on samples and imaged with the Li-Cor Odyssey instrumentation and software. Densitometry was performed on the DNA concentration course experiments using the Li-Cor Odyssey software.

Protein purification resulted in strong Coomassie-stained gel bands between 50 and 75 kilodaltons for both Purα and Purβ. Western procedure showed strong gel bands in the same location when treated with both anti-Purα/Purβ and anti-GST. (FIG. 12). Silver staining after RNAse treatment confirmed the presence of Purα and Purβ in the elution used for EMSA procedures.

Figure 13:
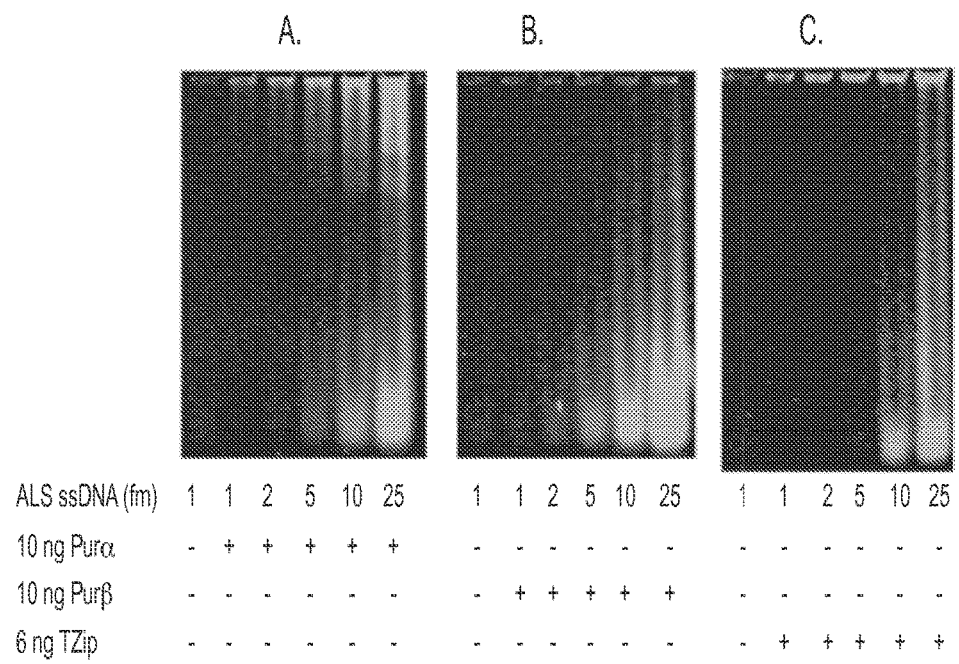
FIG. 13 shows Electrophoretic Mobility Shift Assays (EMSA) with Purα, Purβ, and TZIP on 4% TBE polyacrylamide gels.

DNA concentration courses demonstrated that Purα and TZIP both strongly bind the ALS repeat in low concentrations. FIG. 13 shows Electrophoretic Mobility Shift Assays (EMSA) with Purα, Purβ, and TZIP on 4% TBE polyacrylamide gels. FIG. 13A shows constant Purα with ALS ssDNA alone. FIG. 13B shows constant Purβ with ALS ssDNA alone. FIG. 13C shows constant TZIP with ALS ssDNA alone. Densitometry revealed a $K_d$ value of $1.6 \times 10^{-8}$ for Purα to ALS repeat and $5.5 \times 10^{10}$ for TZIP to ALS repeat. Purβ bound the ALS repeat to a much smaller degree. A $K_d$ value obtained for Purβ was complex and not readily interpretable.

Figure 14:
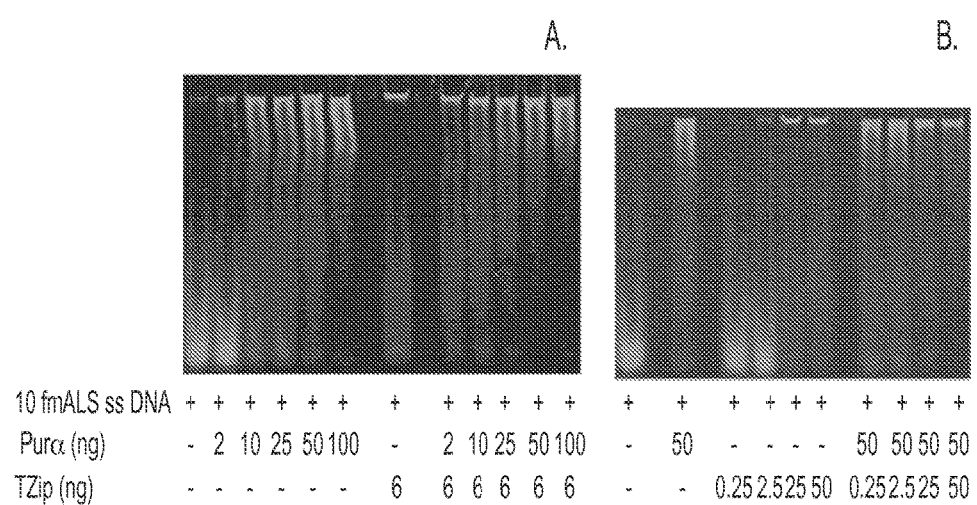
FIGS. 14 A and B provide EMSA with Purα and TZIP combined in a reaction mixture with IR-labeled ssDNA ALS being held constant.

Purα and TZIP mixed demonstrated the ability of TZIP to alter the binding activity of Purα (FIG. 14—A). Increasing the concentrations of TZIP causes the shifted band to migrate more slowly (FIG. 14—B).

Figure 15:
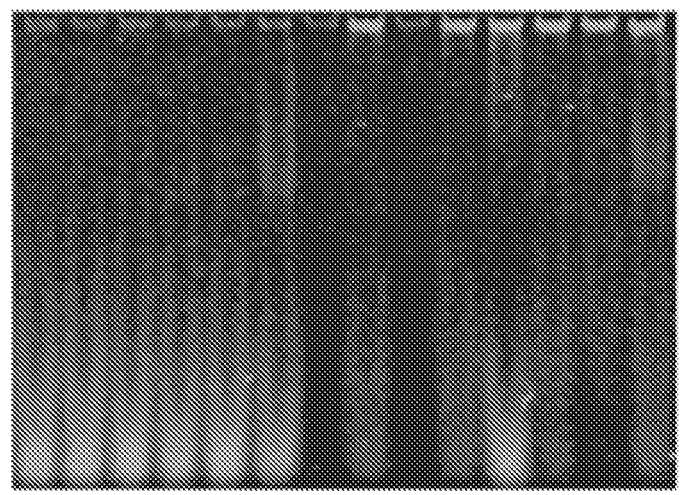
FIG. 15 shows EMSA with Purβ and TZIP combined in reaction mixture with Purβ concentrations being varied while TZIP and IR-labeled ssDNA ALS concentrations were held constant.
Figure 16:
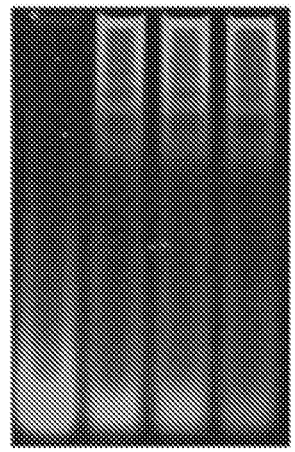
FIG. 16 shows EMSA with Purα and Purβ combined in reaction mixture and Purα and IR-labeled ssDNA ALS concentrations were held constant while Purβ concentrations were varied.

When Purβ and TZIP are mixed, a very different effect is seen. TZIP greatly stimulates binding of Purβ to the ALS hexanucleotide repeat (FIG. 15). Varying amounts of Purβ seem to have different effects, ranging from apparent inhibition of binding to enhancement of TZIP's binding. This effect is not seen when Pur 0 is mixed with Purα, though other constructs of DNA may show this relationship. Increasing Purβ appears to shift more of the oligonucleotide. FIG. 16 shows EMSA with Purα and Purβ combined in reaction mixture and Purα and IR-labeled ssDNA ALS concentrations were held constant while Purβ concentrations were varied.

Example 11

A GE Microspin GST purification module was used to purify GST-tagged Purα and Purβ from bacterial lysate. Polyacrylamide gel electrophoresis with SDS-Page gels and molecular markers were used to verify that GST, Purα, and Purβ were expressed and purified. Expressed proteins were detected using antibodies against Purα and Purβ, including monoclonal mouse anti-Pur antibody developed in Johnson laboratory (clone 10B12) and polyclonal antibody against Purβ (Abcam). Polyacrylamide gel electrophoresis with TBE buffer was used for gel-mobility shift assay.

Infrared-labeled oligonucleotides representing G-rich trinucleotide DNA repeats at FMR1 in patients with Fragile X Syndrome (FXS) were custom ordered and are referred to herein as FXS ssDNA. Infrared-labeled oligonucleotide substrates in agarose and polyacrylamide gels were detected through the use of the Odyssey (LICOR) instrumentation and software.

Figure 17:
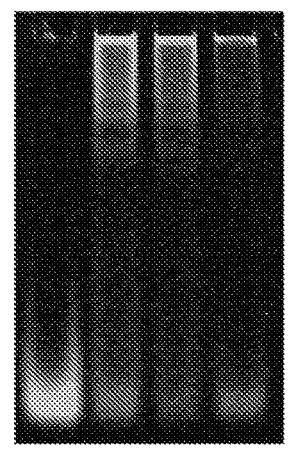
FIG. 17 shows Electrophoretic mobility shift assay with constant ssDNA FXS expanded repeat and constant Purα protein with increasing amounts of Purβ protein.
Figure 18:
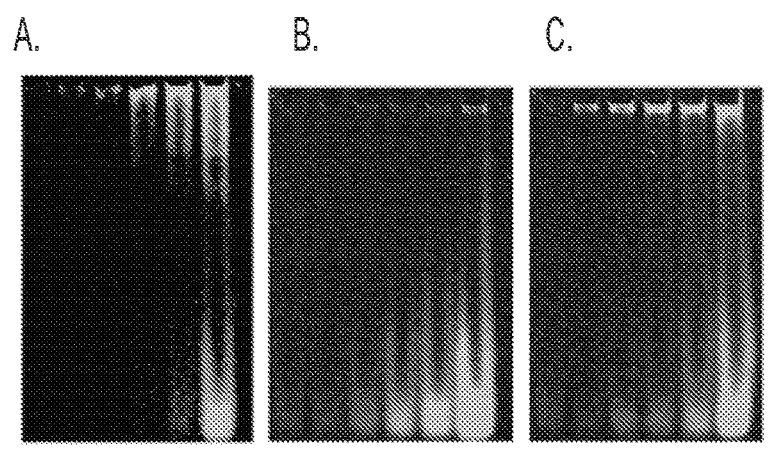
FIG. 18 shows Electrophoretic mobility shift assays for:
(A) Constant Purα protein with increasing amounts of ssDNA FXS;
(B) Constant Purβ protein with increasing amounts of ssDNA FXS;
(C) Constant TZIP peptide with increasing amounts of ssDNA FXS.
Figure 19:
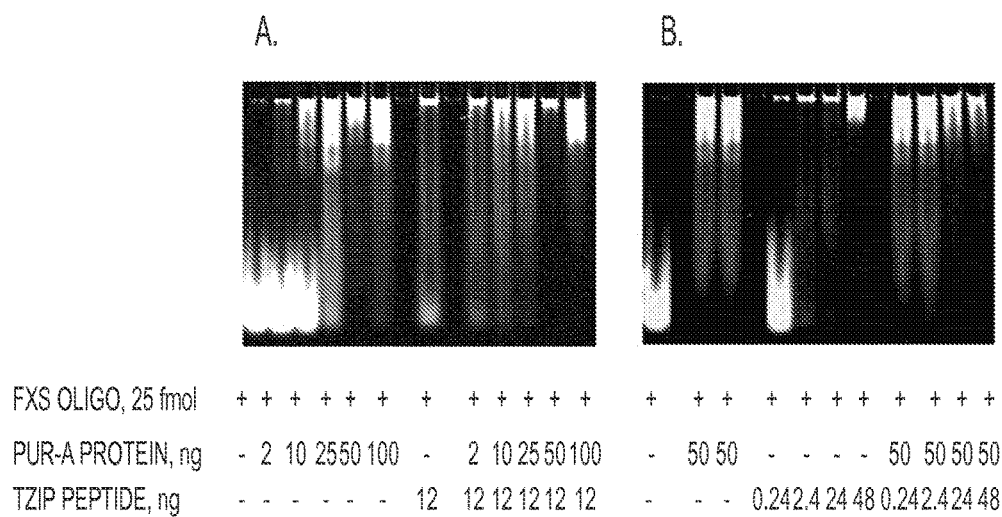
FIG. 19 shows Electrophoretic mobility shift assays for:
(A) Constant ssDNA FXS with increasing amounts of Purα protein as well as constant ssDNA FXS and constant TZIP peptide with increasing amounts of Purα protein;
(B) Constant ssDNA FXS with increasing amounts of TZIP peptide as well as constant ssDNA FXS and constant Purα protein with increasing amounts of TZIP peptide.

The protein gels show that after the purification of Purα and Purβ from bacterial lysates, these Pur proteins are present with only limited contaminants. When Purα and Purβ are combined (FIG. 17), by increasing the amount of Purβ, the DNA is shifted more to the top of the gel. Therefore, there is more binding of the proteins to the DNA. The mobility shift in FIG. 18 shows that as ssDNA FXS is increased up to 50 ng, more than 10 ng of Purα or Purβ is needed to cause a complete shift in mobility. Purβ does not shift the ssDNA FXS as strongly as Purα. FIGS. 18 and 19 show that TZIP works very similarly to Purα in that it moves more ssDNA FXS to the top of the gel as more TZIP is added. In FIG. 19, TZIP enhances the mobility shift of ssDNA FXS in the presence of Purα. TZIP tightly binds the FXS trinucleotide expanded repeat and greatly stimulates Purα binding.

TZIP may work as an agonist to Purα. Less TZIP than Purα is needed to cause the mobility shift. Densitometry revealed a $K_d$ value of $1.9 \times 10^9$ for Purα and $9.5 \times 10^{10}$ for TZIP. The order of binding ssDNA FXS in these experiments is, therefore: TZIP>Purα>Purβ. If TZIP were to work in a very similar way as Purα and Purβ in cells, its addition could take the place of the Pur proteins by binding to the DNA, freeing up the PUR proteins to proceed with their normal functions.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. For example, the disclosed peptide, and variants thereof, can be used to treat or prevent cancers, tumors, and diseases with amplified c-MYC genes including, but not limited to, SCLC, prostate cancer, cancers of the colon, head and neck, mesothelioma, lymphoma, various brain tumors, bladder cancer, AML and malignant melanoma. The agents are also useful in the treatment of, and prevention of transmission of, HIV and treatment of expanded nucleotide repeat diseases, including certain currently untreatable and debilitating diseases. Further, the residues of the disclosed amino acid sequence can be substituted provided that those substitutions allow the peptide to be soluble in aqueous solution, bind to RB and sequences upstream of the c-MYC gene, be transported in and out of cells, and recruit cell cycle regulatory proteins. Moreover, equivalent routes of administration that enable the peptide to enter cells can be used to administer the therapeutic agent. The scope of the invention is as set forth in the appended claims and equivalents thereof, rather than being limited to the examples contained in the foregoing description. The contents of all of the references disclosed herein are incorporated by reference in their entirety.

What is claimed is:

1. A peptide comprising the amino acid sequence LASTFVTRDNKRYFMDLKENQRGRFMRVSQVGTRGYRNSLTVSYSVAWLEFRTHLCKLID EYAKLQYARAKRRQARRQIRQQQQQQQEE (SEQ ID NO: 1).

2. The peptide of claim 1, consisting of the amino acid sequence LASTFVTRDNKRYFMDLKENQRGRFMRVSQVGTRGYRNSLTVSYSVAWLEFR THLCKLIDEYAKLQYARAKRRQARRQIRQQQQQQQEE (SEQ ID NO: 1).

3. A method for modulating the proliferation of cells comprising administering a therapeutically effective amount of a therapeutic agent comprising the amino acid sequence LASTFVTRDNKRYFMDLKENQRGRFMRVSQVGTRGYRNSLTVSYSV AWLEFRTHLCKLIDEYAKLQYARAKRRQARRQIRQQQQQQQEE (SEQ ID NO: 1) and a pharmaceutically acceptable carrier.

4. A pharmaceutical composition comprising a peptide comprising the amino acid sequence LASTFVTRDNKRYFMDLKENQRGRFMRVSQVGTRGY RNSLTVSYSVAWLEFRTHLCKLIDEYAKLQYARAKRRQARRQIRQQQQQQQEE (SEQ ID NO: 1) and a pharmaceutically acceptable carrier.

5. The pharmaceutical composition of claim 4 in the form of a cream.

* * * * *